United States Patent
Nawana et al.

(10) Patent No.: US 11,964,121 B2
(45) Date of Patent: Apr. 23, 2024

(54) MONO DOSE DERMAL PATCH FOR PHARMACEUTICAL DELIVERY

(71) Applicant: Satio, Inc., Boston, MA (US)

(72) Inventors: Namal Nawana, Weston, MA (US); Ziad Tarik Al-Shamsie, San Diego, CA (US)

(73) Assignee: Satio, Inc.

( * ) Notice: Subject to any disclaimer, the term of this patent is extended or adjusted under 35 U.S.C. 154(b) by 0 days.

(21) Appl. No.: 17/500,873

(22) Filed: Oct. 13, 2021

(65) Prior Publication Data

US 2023/0109881 A1   Apr. 13, 2023

(51) Int. Cl.
  *A61M 37/00*   (2006.01)

(52) U.S. Cl.
  CPC .  *A61M 37/0015* (2013.01); *A61M 2037/0023* (2013.01); *A61M 2037/0046* (2013.01); *A61M 2037/0061* (2013.01)

(58) Field of Classification Search
  CPC ...... A61M 37/0015; A61M 2037/0023; A61M 2037/0046; A61M 2037/0061
  USPC .......................................................... 604/22
  See application file for complete search history.

(56) References Cited

U.S. PATENT DOCUMENTS

| | | | |
|---|---|---|---|
| 5,015,228 A | 5/1991 | Columbus et al. | |
| 5,338,308 A | 8/1994 | Wilk | |
| 5,441,490 A | 8/1995 | Svedman | |
| 5,527,288 A | 6/1996 | Gross et al. | |
| 5,602,037 A | 2/1997 | Ostgaard et al. | |
| 5,636,640 A | 6/1997 | Staehlin | |
| 5,680,872 A | 10/1997 | Sesekura et al. | |
| 5,848,991 A | 12/1998 | Gross et al. | |
| 5,997,501 A * | 12/1999 | Gross ................. | A61M 5/14248 604/65 |
| 6,234,980 B1 | 5/2001 | Bell | |
| 6,315,985 B1 | 11/2001 | Wu et al. | |
| 6,454,140 B1 | 9/2002 | Jinks | |
| 6,500,150 B1 | 12/2002 | Gross et al. | |
| 6,506,168 B1 | 1/2003 | Fathallah et al. | |
| 6,524,284 B1 | 2/2003 | Marshall | |
| 6,610,273 B2 | 8/2003 | Wu et al. | |
| 6,623,457 B1 | 9/2003 | Rosenberg | |

(Continued)

FOREIGN PATENT DOCUMENTS

| | | |
|---|---|---|
| AU | 2006283345 A1 | 3/2007 |
| AU | 2016266112 A1 | 12/2016 |

(Continued)

OTHER PUBLICATIONS

U.S. Appl. No. 17/412,205, filed Aug. 25, 2021, Namal Nawana.

(Continued)

*Primary Examiner* — Phillip A Gray
(74) *Attorney, Agent, or Firm* — Potomac Law Group, PLLC; John J. Penny, Jr.

(57) ABSTRACT

A method for delivery of a pharmaceutical to a subject includes applying a dermal patch to a subject's skin, wherein the dermal patch comprises a reservoir that stores a pharmaceutical and further comprises at least one hollow needle configured for puncturing the skin, actuating the at least one needle to puncture the subject's skin, and causing at least a portion of the stored pharmaceutical to be released from the reservoir for delivery via a lumen of the hollow needle to the subject.

29 Claims, 28 Drawing Sheets

(56) References Cited

U.S. PATENT DOCUMENTS

| | | |
|---|---|---|
| 6,644,517 B2 | 11/2003 | Thiel et al. |
| 6,689,118 B2 | 2/2004 | Alchas et al. |
| 6,776,776 B2 | 8/2004 | Alchas et al. |
| 6,780,171 B2 | 8/2004 | Gabel et al. |
| 6,796,429 B2 | 9/2004 | Cameron et al. |
| 6,808,506 B2 | 10/2004 | Lastovich et al. |
| 6,893,655 B2 | 5/2005 | Flanigan et al. |
| 6,932,082 B2 | 8/2005 | Stein |
| 6,960,193 B2 | 11/2005 | Rosenberg |
| 6,994,691 B2 | 2/2006 | Ejlersen |
| 7,004,928 B2 | 2/2006 | Aceti et al. |
| 7,083,592 B2 | 8/2006 | Lastovich et al. |
| 7,101,534 B1 | 9/2006 | Schultz et al. |
| 7,156,838 B2 | 1/2007 | Gabel et al. |
| 7,175,642 B2 | 2/2007 | Briggs et al. |
| 7,182,955 B2 | 2/2007 | Hart et al. |
| 7,250,037 B2 | 7/2007 | Shermer et al. |
| 7,252,651 B2 | 8/2007 | Haider et al. |
| 7,282,058 B2 | 10/2007 | Levin et al. |
| 7,308,893 B2 | 12/2007 | Boot |
| 7,435,415 B2 | 10/2008 | Gelber |
| 7,637,891 B2 * | 12/2009 | Wall .................. A61M 5/422 604/93.01 |
| 7,651,475 B2 | 1/2010 | Angel et al. |
| 7,678,079 B2 | 3/2010 | Shermer et al. |
| 7,846,488 B2 | 12/2010 | Johnson et al. |
| 7,905,866 B2 | 3/2011 | Haider et al. |
| 8,048,019 B2 | 11/2011 | Nisato et al. |
| 8,057,842 B2 | 11/2011 | Choi et al. |
| 8,066,680 B2 | 11/2011 | Alchas et al. |
| 8,079,960 B2 | 12/2011 | Briggs et al. |
| 8,104,469 B2 | 1/2012 | Dams |
| 8,108,023 B2 | 1/2012 | Mir et al. |
| 8,157,768 B2 | 4/2012 | Haider et al. |
| 8,206,336 B2 | 6/2012 | Shantha |
| 8,246,582 B2 | 8/2012 | Angel et al. |
| 8,246,893 B2 | 8/2012 | Ferguson et al. |
| 8,252,268 B2 | 8/2012 | Slowey et al. |
| 8,267,889 B2 | 9/2012 | Cantor et al. |
| 8,303,518 B2 | 11/2012 | Aceti et al. |
| D681,195 S | 4/2013 | Skulley et al. |
| 8,409,140 B2 | 4/2013 | Ejlersen et al. |
| 8,414,503 B2 | 4/2013 | Briggs et al. |
| 8,414,959 B2 | 4/2013 | Hye-Ok et al. |
| 8,430,097 B2 | 4/2013 | Jinks et al. |
| 8,459,253 B2 | 6/2013 | Howgill |
| 8,491,500 B2 | 7/2013 | Briggs et al. |
| 8,496,601 B2 | 7/2013 | Briggs et al. |
| D687,550 S | 8/2013 | Moeckly et al. |
| D687,551 S | 8/2013 | Moeckly et al. |
| D687,945 S | 8/2013 | Brewer et al. |
| D687,946 S | 8/2013 | Brewer et al. |
| D687,947 S | 8/2013 | Brewer et al. |
| 8,512,244 B2 | 8/2013 | Jennewine |
| 8,517,019 B2 | 8/2013 | Brewer et al. |
| 8,554,317 B2 | 10/2013 | Duan |
| 8,556,861 B2 | 10/2013 | Tsals |
| 8,561,795 B2 | 10/2013 | Schott |
| D693,921 S | 11/2013 | Burton et al. |
| 8,602,271 B2 | 12/2013 | Winker et al. |
| 8,603,040 B2 | 12/2013 | Haider et al. |
| 8,608,889 B2 | 12/2013 | Sever et al. |
| 8,622,963 B2 | 1/2014 | Iwase et al. |
| 8,696,619 B2 | 4/2014 | Schnall |
| 8,696,637 B2 | 4/2014 | Ross |
| D705,422 S | 5/2014 | Burton et al. |
| 8,715,232 B2 | 5/2014 | Yodfat et al. |
| 8,740,014 B2 | 6/2014 | Purkins et al. |
| 8,741,377 B2 | 6/2014 | Choi et al. |
| 8,784,363 B2 | 7/2014 | Frederickson et al. |
| 8,808,202 B2 | 8/2014 | Brancazio |
| 8,808,786 B2 | 8/2014 | Jinks et al. |
| 8,814,009 B2 | 8/2014 | Hodson et al. |
| 8,814,035 B2 | 8/2014 | Stuart |
| 8,821,412 B2 | 9/2014 | Gonzalez-Zugasti et al. |
| 8,821,446 B2 | 9/2014 | Trautman et al. |
| 8,821,779 B2 | 9/2014 | Ferguson et al. |
| 8,827,971 B2 | 9/2014 | Gonzalez-Zugasti et al. |
| 8,870,821 B2 | 10/2014 | Laufer |
| 8,900,180 B2 | 12/2014 | Wolter et al. |
| 8,900,194 B2 | 12/2014 | Clarke et al. |
| 8,945,071 B2 | 2/2015 | Christensen |
| 8,961,431 B2 | 2/2015 | Roe et al. |
| 9,022,973 B2 | 5/2015 | Sexton et al. |
| 9,033,898 B2 | 5/2015 | Chickering, III et al. |
| 9,041,541 B2 | 5/2015 | Levinson et al. |
| D733,290 S | 6/2015 | Burton et al. |
| 9,067,031 B2 | 6/2015 | Jinks et al. |
| 9,072,664 B2 | 7/2015 | Stein et al. |
| 9,089,661 B2 | 7/2015 | Stuart et al. |
| 9,089,677 B2 | 7/2015 | Soo et al. |
| 9,113,836 B2 | 8/2015 | Bernstein et al. |
| 9,119,578 B2 | 9/2015 | Haghgooie et al. |
| 9,119,945 B2 | 9/2015 | Simons et al. |
| 9,133,024 B2 | 9/2015 | Phan et al. |
| 9,144,651 B2 | 9/2015 | Stuart |
| 9,144,671 B2 | 9/2015 | Cantor et al. |
| 9,173,994 B2 | 11/2015 | Ziaie et al. |
| 9,174,035 B2 | 11/2015 | Ringsred et al. |
| 9,186,097 B2 | 11/2015 | Frey et al. |
| 9,227,021 B2 | 1/2016 | Buss |
| 9,289,763 B2 | 3/2016 | Berthier et al. |
| 9,289,925 B2 | 3/2016 | Ferguson et al. |
| 9,289,968 B2 | 3/2016 | Sever et al. |
| 9,295,417 B2 | 3/2016 | Haghgooie et al. |
| 9,295,987 B2 | 3/2016 | Kelly et al. |
| 9,339,956 B2 | 5/2016 | Rendon |
| 9,380,972 B2 | 7/2016 | Fletcher et al. |
| 9,380,973 B2 | 7/2016 | Fletcher et al. |
| 9,468,404 B2 | 10/2016 | Hayden |
| 9,480,428 B2 | 11/2016 | Colin et al. |
| 9,504,813 B2 | 11/2016 | Buss |
| 9,522,225 B2 | 12/2016 | Chong et al. |
| 9,549,700 B2 | 1/2017 | Fletcher et al. |
| 9,555,187 B2 | 1/2017 | Sonderegger et al. |
| 9,566,393 B2 | 2/2017 | Iwase et al. |
| 9,579,461 B2 | 2/2017 | Sonderegger et al. |
| 9,623,087 B2 | 4/2017 | Zhang et al. |
| 9,642,895 B2 | 5/2017 | Dai et al. |
| 9,643,229 B2 | 5/2017 | Wilson et al. |
| 9,675,675 B2 | 6/2017 | Zhang et al. |
| 9,675,752 B2 | 6/2017 | Christensen |
| 9,682,222 B2 | 6/2017 | Burton et al. |
| 9,693,950 B2 | 7/2017 | Determan et al. |
| 9,694,149 B2 | 7/2017 | Jinks et al. |
| 9,717,850 B2 | 8/2017 | Sonderegger |
| 9,724,462 B2 | 8/2017 | Rotem |
| 9,730,624 B2 | 8/2017 | Gonzalez-Zugasti et al. |
| 9,770,578 B2 | 9/2017 | Chowdhury |
| 9,775,551 B2 | 10/2017 | Bernstein et al. |
| 9,782,574 B2 | 10/2017 | Simmers |
| 9,789,249 B2 | 10/2017 | Frederickson et al. |
| 9,789,299 B2 | 10/2017 | Simmers |
| 9,844,631 B2 | 12/2017 | Bureau |
| 9,849,270 B2 | 12/2017 | Stockholm |
| D808,515 S | 1/2018 | Atkin et al. |
| 9,861,580 B2 | 1/2018 | Mueting et al. |
| 9,861,801 B2 | 1/2018 | Baker et al. |
| 9,872,975 B2 | 1/2018 | Burton et al. |
| 9,884,151 B2 | 2/2018 | Sullivan et al. |
| 9,895,520 B2 | 2/2018 | Burton et al. |
| 9,956,170 B2 | 5/2018 | Cantor et al. |
| 9,968,767 B1 | 5/2018 | Hasan et al. |
| 9,987,629 B2 | 6/2018 | Berthier et al. |
| 9,993,189 B2 | 6/2018 | Phan et al. |
| 10,004,887 B2 | 6/2018 | Gross et al. |
| 10,010,676 B2 | 7/2018 | Bureau |
| 10,010,706 B2 | 7/2018 | Gonzalez et al. |
| 10,010,707 B2 | 7/2018 | Colburn et al. |
| 10,016,315 B2 | 7/2018 | Letourneau et al. |
| 10,029,845 B2 | 7/2018 | Jinks |
| 10,035,008 B2 | 7/2018 | Brandwein et al. |
| 10,076,649 B2 | 9/2018 | Gilbert et al. |
| 10,080,843 B2 | 9/2018 | Bureau |

(56) References Cited

U.S. PATENT DOCUMENTS

| | | |
|---|---|---|
| 10,080,846 B2 | 9/2018 | Sonderegger et al. |
| 10,099,043 B2 | 10/2018 | Berry et al. |
| 10,105,524 B2 | 10/2018 | Meyer et al. |
| 10,111,807 B2 | 10/2018 | Baker et al. |
| D834,704 S | 11/2018 | Atkin et al. |
| 10,154,957 B2 | 12/2018 | Zhang et al. |
| 10,155,334 B2 | 12/2018 | Rendon |
| 10,183,156 B2 | 1/2019 | Ross et al. |
| 10,188,335 B2 | 1/2019 | Haghgooie et al. |
| D840,020 S | 2/2019 | Howgill |
| 10,201,691 B2 | 2/2019 | Berry et al. |
| 10,232,157 B2 | 3/2019 | Berry et al. |
| 10,232,160 B2 | 3/2019 | Baker et al. |
| 10,248,765 B1 | 4/2019 | Holmes et al. |
| 10,265,484 B2 | 4/2019 | Stuart et al. |
| 10,272,214 B2 | 4/2019 | Child et al. |
| 10,300,260 B2 | 5/2019 | Wirtanen et al. |
| 10,307,578 B2 | 6/2019 | Frederickson et al. |
| 10,315,021 B2 | 6/2019 | Frederickson et al. |
| 10,327,990 B2 | 6/2019 | Egeland et al. |
| 10,328,248 B2 | 6/2019 | Baker et al. |
| 10,335,560 B2 | 7/2019 | Stein et al. |
| 10,335,562 B2 | 7/2019 | Jinks et al. |
| 10,335,563 B2 | 7/2019 | Brewer et al. |
| 10,357,610 B2 | 7/2019 | Sonderegger |
| 10,384,047 B2 | 8/2019 | Simmers |
| 10,391,290 B2 | 8/2019 | Burton et al. |
| 10,398,885 B2 | 9/2019 | Frits et al. |
| 10,406,339 B2 | 9/2019 | Simmers |
| 10,410,838 B2 | 9/2019 | Hanson et al. |
| 10,426,390 B2 | 10/2019 | Berthier et al. |
| 10,426,739 B2 | 10/2019 | Knutson |
| 10,478,346 B2 | 11/2019 | Knutson |
| 10,492,716 B2 | 12/2019 | Berthier et al. |
| 10,507,286 B2 | 12/2019 | Egeland et al. |
| 10,518,071 B2 | 12/2019 | Kulkarni |
| D872,853 S | 1/2020 | Stuart et al. |
| 10,525,463 B2 | 1/2020 | Kelly et al. |
| 10,542,922 B2 | 1/2020 | Sia et al. |
| 10,543,310 B2 | 1/2020 | Bernstein et al. |
| 10,549,079 B2 | 2/2020 | Burton et al. |
| 10,568,937 B2 | 2/2020 | Hattersley et al. |
| D878,544 S | 3/2020 | Stuart et al. |
| 10,576,257 B2 | 3/2020 | Berry et al. |
| 10,596,333 B2 | 3/2020 | Howgill |
| 10,598,583 B1 | 3/2020 | Peeters et al. |
| 10,638,963 B2 | 5/2020 | Beyerlein et al. |
| 10,646,703 B2 | 5/2020 | Chowdhury |
| 10,653,349 B2 | 5/2020 | Delamarche et al. |
| 10,695,289 B2 | 6/2020 | Brown et al. |
| 10,695,547 B2 | 6/2020 | Burton et al. |
| 10,716,926 B2 | 7/2020 | Burton et al. |
| 10,729,842 B2 * | 8/2020 | Hooven ............... A61M 5/145 |
| 10,772,550 B2 | 9/2020 | Aceti et al. |
| 10,779,757 B2 | 9/2020 | Berthier et al. |
| 10,799,166 B2 | 10/2020 | Gonzalez-Zugasti et al. |
| 10,835,163 B2 | 11/2020 | Haghgooie et al. |
| 10,881,342 B2 | 1/2021 | Kelly et al. |
| 10,888,259 B2 | 1/2021 | Jordan et al. |
| 10,926,030 B2 | 2/2021 | Lanigan et al. |
| 10,932,710 B2 | 3/2021 | Jordan et al. |
| 10,939,860 B2 | 3/2021 | Levinson et al. |
| 10,940,085 B2 | 3/2021 | Baker et al. |
| 10,953,211 B2 | 3/2021 | Ross et al. |
| 11,020,548 B2 | 6/2021 | Stuart et al. |
| 11,033,212 B2 | 6/2021 | Berthier et al. |
| 11,040,183 B2 | 6/2021 | Baker et al. |
| 11,103,685 B2 | 8/2021 | Gonzalez et al. |
| 11,110,234 B2 | 9/2021 | Richardson et al. |
| 11,116,953 B2 | 9/2021 | Kobayashi et al. |
| 11,147,955 B2 | 10/2021 | Gross et al. |
| 11,177,029 B2 | 11/2021 | Levinson et al. |
| 11,197,625 B1 | 12/2021 | Schleicher et al. |
| 11,202,895 B2 | 12/2021 | Davis et al. |
| 11,207,477 B2 | 12/2021 | Hodson |
| 11,247,033 B2 | 2/2022 | Baker et al. |
| 11,253,179 B2 | 2/2022 | Bernstein et al. |
| 11,266,337 B2 | 3/2022 | Jackson et al. |
| 11,273,272 B2 | 3/2022 | Stuart et al. |
| 11,291,989 B2 | 4/2022 | Morrison |
| 11,298,060 B2 | 4/2022 | Jordan et al. |
| 11,298,478 B2 | 4/2022 | Stuart et al. |
| 11,304,632 B2 | 4/2022 | Mou et al. |
| 11,344,684 B2 | 5/2022 | Richardson et al. |
| 11,395,614 B2 | 7/2022 | Berthier et al. |
| 11,452,474 B1 | 9/2022 | Nawana et al. |
| 11,458,289 B2 | 10/2022 | Moeckly et al. |
| 11,497,712 B2 | 11/2022 | Stein et al. |
| 11,497,866 B2 | 11/2022 | Howgill |
| 11,510,602 B1 | 11/2022 | Nawana et al. |
| 2002/0077584 A1 | 6/2002 | Lin et al. |
| 2002/0193740 A1 | 12/2002 | Alchas et al. |
| 2004/0002121 A1 | 1/2004 | Regan et al. |
| 2004/0010207 A1 | 1/2004 | Flaherty et al. |
| 2004/0059256 A1 | 3/2004 | Perez |
| 2004/0059366 A1 | 3/2004 | Sato et al. |
| 2004/0106904 A1 | 6/2004 | Gonnelli et al. |
| 2004/0162467 A1 | 8/2004 | Cook |
| 2005/0106713 A1 | 5/2005 | Phan et al. |
| 2005/0118388 A1 | 6/2005 | Kingsford |
| 2006/0047243 A1 | 3/2006 | Rosenberg |
| 2006/0068490 A1 | 3/2006 | Tang et al. |
| 2006/0142651 A1 | 6/2006 | Brister et al. |
| 2007/0004989 A1 | 1/2007 | Dhillon |
| 2007/0191696 A1 | 8/2007 | Mischler et al. |
| 2008/0003274 A1 | 1/2008 | Kaiser |
| 2008/0287864 A1 | 11/2008 | Rosenberg |
| 2009/0012472 A1 | 1/2009 | Ahm et al. |
| 2009/0036826 A1 | 2/2009 | Sage, Jr. et al. |
| 2009/0099427 A1 | 4/2009 | Jina et al. |
| 2009/0112125 A1 | 4/2009 | Tamir |
| 2009/0198215 A1 | 8/2009 | Chong et al. |
| 2009/0259176 A1 | 10/2009 | Yairi |
| 2010/0198107 A1 | 8/2010 | Groll et al. |
| 2010/0249560 A1 | 9/2010 | Levinson et al. |
| 2010/0256524 A1 | 10/2010 | Levinson et al. |
| 2010/0269837 A1 | 10/2010 | Levinson et al. |
| 2010/0272652 A1 | 10/2010 | Levinson |
| 2011/0009847 A1 | 1/2011 | Levinson et al. |
| 2011/0060280 A1 | 3/2011 | Caffey et al. |
| 2011/0105872 A1 | 5/2011 | Chickering, III et al. |
| 2011/0105951 A1 | 5/2011 | Bernstein et al. |
| 2011/0105952 A1 | 5/2011 | Bernstein et al. |
| 2011/0125058 A1 | 5/2011 | Levinson et al. |
| 2011/0144463 A1 | 6/2011 | Pesach et al. |
| 2011/0172508 A1 | 7/2011 | Chickering, III et al. |
| 2011/0172510 A1 | 7/2011 | Chickering, III et al. |
| 2011/0198221 A1 | 8/2011 | Angelescu |
| 2011/0213335 A1 | 9/2011 | Burton et al. |
| 2011/0245635 A1 | 10/2011 | Fujiwara et al. |
| 2011/0257497 A1 | 10/2011 | Tamada et al. |
| 2011/0288389 A9 | 11/2011 | Levinson et al. |
| 2012/0016308 A1 | 1/2012 | Schott |
| 2012/0041338 A1 | 2/2012 | Chickering et al. |
| 2012/0046203 A1 | 2/2012 | Walsh et al. |
| 2012/0078224 A1 | 3/2012 | Lerner et al. |
| 2012/0109066 A1 | 5/2012 | Chase et al. |
| 2012/0123297 A1 | 5/2012 | Brancazio |
| 2012/0259599 A1 | 10/2012 | Deck et al. |
| 2012/0271123 A1 | 10/2012 | Castle et al. |
| 2012/0271125 A1 | 10/2012 | Bernstein et al. |
| 2012/0275955 A1 | 11/2012 | Haghgooie et al. |
| 2012/0277629 A1 | 11/2012 | Bernstein et al. |
| 2012/0277696 A1 | 11/2012 | Gonzalez-Zugasti et al. |
| 2012/0277697 A1 | 11/2012 | Haghgooie et al. |
| 2013/0018279 A1 | 1/2013 | Plante et al. |
| 2013/0158468 A1 | 6/2013 | Bernstein et al. |
| 2013/0158482 A1 | 6/2013 | Davis et al. |
| 2013/0211289 A1 | 8/2013 | Moga et al. |
| 2013/0253446 A1 | 9/2013 | Duan et al. |
| 2013/0269423 A1 | 10/2013 | Angelescu |
| 2014/0066843 A1 | 3/2014 | Zhang et al. |
| 2014/0109900 A1 | 4/2014 | Jinks |
| 2014/0194854 A1 | 7/2014 | Tsals |

(56) References Cited

U.S. PATENT DOCUMENTS

| | | |
|---|---|---|
| 2014/0305823 A1 | 10/2014 | Gelfand et al. |
| 2014/0309555 A1 | 10/2014 | Gelfand et al. |
| 2014/0309557 A1 | 10/2014 | Fletcher et al. |
| 2014/0336616 A1 | 11/2014 | Edwards |
| 2015/0057510 A1 | 2/2015 | Levinson et al. |
| 2015/0057901 A1 | 2/2015 | Sundholm et al. |
| 2015/0073385 A1 | 3/2015 | Lyon et al. |
| 2015/0087944 A1 | 3/2015 | Levinson et al. |
| 2015/0136122 A1 | 5/2015 | Stuart et al. |
| 2015/0250959 A1 | 9/2015 | Stuart et al. |
| 2015/0258272 A1 | 9/2015 | Sullivan et al. |
| 2015/0278476 A1 | 10/2015 | Levinson et al. |
| 2015/0352295 A1 | 12/2015 | Burton et al. |
| 2016/0038068 A1 | 2/2016 | Chickering, III et al. |
| 2016/0051981 A1 | 2/2016 | Berthier et al. |
| 2016/0067468 A1 | 3/2016 | Chowdhury |
| 2016/0136365 A1 | 5/2016 | Stuart et al. |
| 2016/0144100 A1 | 5/2016 | Gharib et al. |
| 2016/0199581 A1 | 7/2016 | Cachemaille et al. |
| 2016/0213295 A1 | 7/2016 | Matsunami et al. |
| 2016/0256095 A1 | 9/2016 | Krasnow et al. |
| 2016/0262676 A1 | 9/2016 | Haghgooie et al. |
| 2016/0315123 A1 | 10/2016 | Kim et al. |
| 2016/0324506 A1 | 11/2016 | Tariyal et al. |
| 2016/0354589 A1 | 12/2016 | Kobayashi et al. |
| 2016/0361006 A1 | 12/2016 | Bullington et al. |
| 2017/0001192 A1 | 1/2017 | Kelly et al. |
| 2017/0014822 A1 | 1/2017 | Ker |
| 2017/0021067 A1 | 1/2017 | Todd et al. |
| 2017/0021117 A1 | 1/2017 | Howgill |
| 2017/0035337 A1 | 2/2017 | Wilkinson et al. |
| 2017/0035975 A1 | 2/2017 | Myung et al. |
| 2017/0043103 A1 | 2/2017 | Wotton et al. |
| 2017/0059304 A1 | 3/2017 | Ma et al. |
| 2017/0120022 A1 | 5/2017 | Chickering, III et al. |
| 2017/0122846 A1 | 5/2017 | Holmes et al. |
| 2017/0127991 A1 | 5/2017 | Bernstein et al. |
| 2017/0173288 A1 | 6/2017 | Stam et al. |
| 2017/0197029 A1 | 7/2017 | Cindrich et al. |
| 2017/0224912 A1 | 8/2017 | Yodfat et al. |
| 2017/0231543 A1 | 8/2017 | Cunningham et al. |
| 2017/0290977 A1 | 10/2017 | Schauderna et al. |
| 2018/0001029 A1 | 1/2018 | Egeland et al. |
| 2018/0008183 A1 | 1/2018 | Chickering, III et al. |
| 2018/0008703 A1 | 1/2018 | Johnson |
| 2018/0008808 A1 | 1/2018 | Chowdhury |
| 2018/0021559 A1 | 1/2018 | Xu |
| 2018/0078241 A1 | 3/2018 | Moga et al. |
| 2018/0103884 A1 | 4/2018 | Delamarche et al. |
| 2018/0126058 A1 | 5/2018 | David et al. |
| 2018/0132515 A1 | 5/2018 | Lawrence et al. |
| 2018/0132774 A1 | 5/2018 | Gonzalez-Zugasti et al. |
| 2018/0242890 A1 | 8/2018 | Chickering, III et al. |
| 2018/0243543 A1 | 8/2018 | Baek et al. |
| 2018/0296148 A1 | 10/2018 | Gelfand et al. |
| 2018/0344631 A1 | 12/2018 | Zhang et al. |
| 2018/0369512 A1 | 12/2018 | Blatchford et al. |
| 2019/0000365 A1 | 1/2019 | Beyerlein et al. |
| 2019/0001076 A1 | 1/2019 | Solomon et al. |
| 2019/0001081 A1 | 1/2019 | Guion et al. |
| 2019/0001085 A1 | 1/2019 | Cottenden et al. |
| 2019/0015584 A1 | 1/2019 | Meehan et al. |
| 2019/0015827 A1 | 1/2019 | Berthier et al. |
| 2019/0022339 A1 | 1/2019 | Richardson et al. |
| 2019/0023473 A1 | 1/2019 | Schott |
| 2019/0030260 A1 | 1/2019 | Wotton et al. |
| 2019/0053740 A1 | 2/2019 | Bernstein et al. |
| 2019/0054010 A1 | 2/2019 | Slowey et al. |
| 2019/0142318 A1 | 5/2019 | Diebold et al. |
| 2019/0159709 A1 | 5/2019 | Barone et al. |
| 2019/0209820 A1 | 7/2019 | Chickering, III et al. |
| 2019/0240470 A1 | 8/2019 | Frederickson et al. |
| 2019/0298943 A1 | 10/2019 | Stuart et al. |
| 2019/0336058 A1 | 11/2019 | Haghgooie et al. |
| 2019/0366067 A1 | 12/2019 | Ginggen et al. |
| 2020/0009364 A1 | 1/2020 | Amir |
| 2020/0010219 A1 | 1/2020 | Felippone et al. |
| 2020/0011860 A1 | 1/2020 | Nawana et al. |
| 2020/0033008 A1 | 1/2020 | Baker |
| 2020/0069897 A1 | 3/2020 | Hodson et al. |
| 2020/0085414 A1 | 3/2020 | Berthier et al. |
| 2020/0101219 A1 | 4/2020 | Wang et al. |
| 2020/0147209 A1 | 5/2020 | Johnson |
| 2020/0163603 A1 | 5/2020 | Jordan et al. |
| 2020/0164359 A1 | 5/2020 | Jordan et al. |
| 2020/0246560 A1 | 8/2020 | Hodson et al. |
| 2020/0253521 A1 | 8/2020 | Ivosevic et al. |
| 2020/0261668 A1 | 8/2020 | Hodson et al. |
| 2020/0289808 A1 | 9/2020 | Moeckly et al. |
| 2020/0297945 A1 | 9/2020 | Cottenden et al. |
| 2020/0353155 A1 | 11/2020 | Bernstein et al. |
| 2021/0022681 A1 | 1/2021 | Chickering, III et al. |
| 2021/0030975 A1 | 2/2021 | Burton et al. |
| 2021/0059588 A1 | 3/2021 | Welch et al. |
| 2021/0100487 A1 | 4/2021 | Cho et al. |
| 2021/0121110 A1 | 4/2021 | Kelly et al. |
| 2021/0170153 A1 | 6/2021 | Ross et al. |
| 2021/0196567 A1 | 7/2021 | Baker et al. |
| 2021/0228124 A1 | 7/2021 | Gonzalez-Zugasti et al. |
| 2021/0259599 A1 | 8/2021 | Haghgooie et al. |
| 2021/0298679 A1 | 9/2021 | Pierart |
| 2021/0330227 A1 | 10/2021 | Levinson et al. |
| 2021/0369150 A1 | 12/2021 | Bernstein et al. |
| 2021/0378567 A1 | 12/2021 | Weidemaier et al. |
| 2022/0031211 A1 | 2/2022 | Yakhnich et al. |
| 2022/0058895 A1 | 2/2022 | Han |
| 2022/0062607 A1 | 3/2022 | Davis et al. |
| 2022/0071534 A9 | 3/2022 | Gonzalez-Zugasti et al. |
| 2022/0133192 A1 | 5/2022 | Brancazio |
| 2022/0134072 A1 | 5/2022 | Kosel et al. |
| 2022/0215921 A1 | 7/2022 | Levinson et al. |
| 2022/0218251 A1 | 7/2022 | Jackson et al. |
| 2022/0233117 A1 | 7/2022 | Lee et al. |
| 2022/0249818 A1 | 8/2022 | Chickering, III et al. |
| 2022/0257158 A1 | 8/2022 | Haghgooie et al. |
| 2022/0287642 A1 | 9/2022 | Chickering, III et al. |
| 2022/0313128 A1 | 10/2022 | Bernstein et al. |
| 2022/0330860 A1 | 10/2022 | Nawana |
| 2022/0361784 A1 | 11/2022 | Jordan et al. |
| 2023/0109881 A1 | 4/2023 | Nawana et al. |

FOREIGN PATENT DOCUMENTS

| | | |
|---|---|---|
| CN | 101296752 A | 10/2008 |
| EP | 0931507 A1 | 7/1999 |
| EP | 1769735 A1 | 4/2007 |
| EP | 2493537 A2 | 9/2012 |
| EP | 3513833 A1 | 7/2019 |
| EP | 3490453 B1 | 12/2021 |
| EP | 3962363 A1 | 3/2022 |
| ES | 2550668 T3 | 11/2015 |
| ES | 2565805 T3 | 4/2016 |
| GB | 1492500 A | 11/1977 |
| JP | 2004024164 A | 1/2004 |
| KR | 101857300 B1 | 5/2018 |
| WO | 9311747 A1 | 6/1993 |
| WO | 9929296 A1 | 6/1999 |
| WO | 0078286 A1 | 12/2000 |
| WO | 0210037 A1 | 2/2002 |
| WO | 0226217 A2 | 4/2002 |
| WO | 0232785 A1 | 4/2002 |
| WO | 02083205 A1 | 10/2002 |
| WO | 02083231 A1 | 10/2002 |
| WO | 02083232 A1 | 10/2002 |
| WO | 03002069 A2 | 1/2003 |
| WO | 03030880 A1 | 4/2003 |
| WO | 03035510 A1 | 5/2003 |
| WO | 03066126 A2 | 8/2003 |
| WO | 03084597 A1 | 10/2003 |
| WO | 03086349 A1 | 10/2003 |
| WO | 03086350 A1 | 10/2003 |
| WO | 03089036 A1 | 10/2003 |
| WO | 2004009172 A1 | 1/2004 |
| WO | 2004022133 A2 | 3/2004 |

(56) References Cited

FOREIGN PATENT DOCUMENTS

| | | |
|---|---|---|
| WO | 2004022142 A1 | 3/2004 |
| WO | 2004032990 A2 | 4/2004 |
| WO | 2004039429 A2 | 5/2004 |
| WO | 2004062715 A3 | 10/2004 |
| WO | 2004098576 A1 | 11/2004 |
| WO | 2005006535 A1 | 1/2005 |
| WO | 2005026236 A1 | 3/2005 |
| WO | 2005060441 A2 | 7/2005 |
| WO | 2005014078 A3 | 10/2005 |
| WO | 2005084534 | 10/2005 |
| WO | 2005123173 A1 | 12/2005 |
| WO | 2006016364 A2 | 2/2006 |
| WO | 2006055795 A1 | 5/2006 |
| WO | 2006055799 A1 | 5/2006 |
| WO | 2006055802 A1 | 5/2006 |
| WO | 2006055844 A2 | 5/2006 |
| WO | 2006062848 A1 | 6/2006 |
| WO | 2006062974 A2 | 6/2006 |
| WO | 2006108185 A1 | 10/2006 |
| WO | 2006115663 A2 | 11/2006 |
| WO | 2006135696 A2 | 12/2006 |
| WO | 2007002521 A2 | 1/2007 |
| WO | 2007002522 A1 | 1/2007 |
| WO | 2007002523 A2 | 1/2007 |
| WO | 2007023276 A1 | 3/2007 |
| WO | 2007061781 A1 | 5/2007 |
| WO | 2007064486 A1 | 6/2007 |
| WO | 2007103712 A2 | 9/2007 |
| WO | 2006110723 A3 | 11/2007 |
| WO | 2007124411 A1 | 11/2007 |
| WO | 2008014161 A1 | 1/2008 |
| WO | 2007124406 A3 | 2/2008 |
| WO | 2008008845 A3 | 4/2008 |
| WO | 2008049107 A1 | 4/2008 |
| WO | 2008091602 A3 | 9/2008 |
| WO | 2008121459 A1 | 10/2008 |
| WO | 2008149333 A9 | 1/2009 |
| WO | 2009037192 A1 | 3/2009 |
| WO | 2009046173 A3 | 5/2009 |
| WO | 2009061895 A2 | 5/2009 |
| WO | 2009061907 A2 | 5/2009 |
| WO | 2009056981 A3 | 8/2009 |
| WO | 2009126653 A1 | 10/2009 |
| WO | 2009158300 A1 | 12/2009 |
| WO | 2009142852 A3 | 1/2010 |
| WO | 2010049048 A1 | 5/2010 |
| WO | 2010059605 A2 | 5/2010 |
| WO | 2010062908 A1 | 6/2010 |
| WO | 2010071262 A1 | 6/2010 |
| WO | 2010098339 A1 | 9/2010 |
| WO | 2010101621 A1 | 9/2010 |
| WO | 2010101625 A2 | 9/2010 |
| WO | 2010101626 A1 | 9/2010 |
| WO | 2010101620 A3 | 11/2010 |
| WO | 2010129783 A1 | 11/2010 |
| WO | 2010002613 A3 | 12/2010 |
| WO | 2010110916 A3 | 12/2010 |
| WO | 2010151329 A1 | 12/2010 |
| WO | 2010117602 A3 | 3/2011 |
| WO | 2011016615 A3 | 4/2011 |
| WO | 2011053787 A2 | 5/2011 |
| WO | 2011053788 A2 | 5/2011 |
| WO | 2011053796 A2 | 5/2011 |
| WO | 2011063067 A1 | 5/2011 |
| WO | 2011065972 A2 | 6/2011 |
| WO | 2011071788 A1 | 6/2011 |
| WO | 2011075099 A1 | 6/2011 |
| WO | 2011075103 A1 | 6/2011 |
| WO | 2011075104 A1 | 6/2011 |
| WO | 2011075105 A1 | 6/2011 |
| WO | 2011075569 A1 | 6/2011 |
| WO | 2011084316 A2 | 7/2011 |
| WO | 2011088211 A2 | 7/2011 |
| WO | 2011094573 A1 | 8/2011 |
| WO | 2011014514 | 9/2011 |
| WO | 2011088214 A3 | 9/2011 |
| WO | 2011113114 A1 | 9/2011 |
| WO | 2011116388 A1 | 9/2011 |
| WO | 2011084951 A3 | 11/2011 |
| WO | 2011088211 A3 | 12/2011 |
| WO | 2011150144 A2 | 12/2011 |
| WO | 2011163347 A2 | 12/2011 |
| WO | 2012030316 A1 | 3/2012 |
| WO | 2012018486 A3 | 4/2012 |
| WO | 2012045561 A1 | 4/2012 |
| WO | 2012048388 A1 | 4/2012 |
| WO | 2012049155 A1 | 4/2012 |
| WO | 2012054592 A1 | 4/2012 |
| WO | 2012021792 A3 | 5/2012 |
| WO | 2012028675 A3 | 5/2012 |
| WO | 2012061556 A1 | 5/2012 |
| WO | 2012089627 A1 | 7/2012 |
| WO | 2012122162 A1 | 9/2012 |
| WO | 2012145665 A2 | 10/2012 |
| WO | 2012117302 A3 | 11/2012 |
| WO | 2012149126 A1 | 11/2012 |
| WO | 2012149143 A1 | 11/2012 |
| WO | 2012154362 | 12/2012 |
| WO | 2012173971 A1 | 12/2012 |
| WO | 2012149134 | 1/2013 |
| WO | 2012149155 A9 | 3/2013 |
| WO | 2013036602 A1 | 3/2013 |
| WO | 2013050701 A1 | 4/2013 |
| WO | 2013055638 A1 | 4/2013 |
| WO | 2013055641 A1 | 4/2013 |
| WO | 2013059409 A1 | 4/2013 |
| WO | 2013082418 A1 | 6/2013 |
| WO | 2013082427 A1 | 6/2013 |
| WO | 2013090353 A1 | 6/2013 |
| WO | 2013096026 A1 | 6/2013 |
| WO | 2013096027 A1 | 6/2013 |
| WO | 2013112877 A1 | 8/2013 |
| WO | 2013120665 A1 | 8/2013 |
| WO | 2013136176 A1 | 9/2013 |
| WO | 2013136185 A3 | 11/2013 |
| WO | 2013165715 A1 | 11/2013 |
| WO | 2013188609 A1 | 12/2013 |
| WO | 2014004462 A1 | 1/2014 |
| WO | 2014018558 A1 | 1/2014 |
| WO | 2014039367 A1 | 3/2014 |
| WO | 2014052263 A1 | 4/2014 |
| WO | 2014058746 A1 | 4/2014 |
| WO | 2014059104 A1 | 4/2014 |
| WO | 2014078545 A1 | 5/2014 |
| WO | 2014081746 A1 | 5/2014 |
| WO | 2014099404 A1 | 6/2014 |
| WO | 2014105458 A1 | 7/2014 |
| WO | 2014110016 A1 | 7/2014 |
| WO | 2014096001 A3 | 8/2014 |
| WO | 2014132239 A1 | 9/2014 |
| WO | 2014132240 A1 | 9/2014 |
| WO | 2014153447 A2 | 9/2014 |
| WO | 2014160804 A2 | 10/2014 |
| WO | 2014193725 A1 | 12/2014 |
| WO | 2014193727 A1 | 12/2014 |
| WO | 2014193729 A1 | 12/2014 |
| WO | 2014204951 A1 | 12/2014 |
| WO | 2014186263 A3 | 1/2015 |
| WO | 2015006292 A1 | 1/2015 |
| WO | 2015009523 A1 | 1/2015 |
| WO | 2015009530 A1 | 1/2015 |
| WO | 2015009531 A1 | 1/2015 |
| WO | 2015031552 A1 | 3/2015 |
| WO | 2015034709 A1 | 3/2015 |
| WO | 2015038556 A1 | 3/2015 |
| WO | 2015023649 A3 | 4/2015 |
| WO | 2015072924 A1 | 5/2015 |
| WO | 2015116625 A1 | 8/2015 |
| WO | 2015153570 A1 | 10/2015 |
| WO | 2015153624 A1 | 10/2015 |
| WO | 2015168210 A1 | 11/2015 |
| WO | 2015168215 A1 | 11/2015 |
| WO | 2015168217 A1 | 11/2015 |
| WO | 2015179511 A1 | 11/2015 |

(56) References Cited

FOREIGN PATENT DOCUMENTS

| | | |
|---|---|---|
| WO | 2016009986 A1 | 1/2016 |
| WO | 2016018892 A1 | 2/2016 |
| WO | 2016081843 A1 | 5/2016 |
| WO | 2016099986 A2 | 6/2016 |
| WO | 2016100708 A1 | 6/2016 |
| WO | 2016109336 A1 | 7/2016 |
| WO | 2016109339 A1 | 7/2016 |
| WO | 2016109342 A1 | 7/2016 |
| WO | 2016118459 A1 | 7/2016 |
| WO | 2016122915 A1 | 8/2016 |
| WO | 2016132368 A1 | 8/2016 |
| WO | 2016137853 A1 | 9/2016 |
| WO | 2016164508 A1 | 10/2016 |
| WO | 2015168219 | 12/2016 |
| WO | 2017044887 A1 | 3/2017 |
| WO | 2017062727 A1 | 4/2017 |
| WO | 2017062922 A1 | 4/2017 |
| WO | 2017075018 A1 | 5/2017 |
| WO | 2017075586 A1 | 5/2017 |
| WO | 2017087355 A1 | 5/2017 |
| WO | 2017087368 A1 | 5/2017 |
| WO | 2017112400 A1 | 6/2017 |
| WO | 2017112451 A1 | 6/2017 |
| WO | 2017112452 A1 | 6/2017 |
| WO | 2017112748 A1 | 6/2017 |
| WO | 2017113011 A1 | 7/2017 |
| WO | 2017139084 A1 | 8/2017 |
| WO | 2017112476 A3 | 9/2017 |
| WO | 2017176693 A1 | 10/2017 |
| WO | 2017176704 A1 | 10/2017 |
| WO | 2017193076 A1 | 11/2017 |
| WO | 2018022535 A1 | 2/2018 |
| WO | 2018048786 A1 | 3/2018 |
| WO | 2018048790 A1 | 3/2018 |
| WO | 2018048795 A1 | 3/2018 |
| WO | 2018048797 A1 | 3/2018 |
| WO | 2018057760 A1 | 3/2018 |
| WO | 2018128976 A1 | 7/2018 |
| WO | 2018132515 A1 | 7/2018 |
| WO | 2018204217 A1 | 11/2018 |
| WO | 2018213244 A1 | 11/2018 |
| WO | 2019067567 A1 | 4/2019 |
| WO | 2019121324 A1 | 6/2019 |
| WO | 2020025823 A1 | 2/2020 |
| WO | 2020102281 A1 | 5/2020 |
| WO | 2020223710 A1 | 11/2020 |
| WO | 2021007344 A1 | 1/2021 |
| WO | 2021041881 A1 | 3/2021 |
| WO | 2021076846 A1 | 4/2021 |
| WO | 2021121638 A1 | 6/2021 |
| WO | 2021198768 A2 | 10/2021 |
| WO | 2021222066 A1 | 11/2021 |
| WO | 2021222805 A1 | 11/2021 |
| WO | 2022064055 A1 | 3/2022 |

OTHER PUBLICATIONS

U.S. Appl. No. 17/412,213, filed Aug. 25, 2021, Namal Nawana.
U.S. Appl. No. 17/521,466, filed Nov. 8, 2021, Namal Nawana.
International Search Report and Written Opinion, PCT/US2022/024607, dated Aug. 4, 2022, 17 pages.
English machine translation of JP-2004024164-A, patents.google.com, 8 pages.
International Search Report and Written Opinion, PCT/US2022/029829, dated Nov. 23, 2022, 16 pages.
International Search Report and Written Opinion, PCT/US2022/046384, dated Jan. 5, 2023, 12 pages.
International Search Report and Written Opinion, PCT/US2022/048913, dated Feb. 21, 2023, 16 pages.
Taiwan Office Action, TW111142334, dated May 18, 2023, 15 pages.
International Preliminary Report on Patentability for International Application No. PCT/US2022/024607 dated Oct. 12, 2023.
International Search Report and Written Opinion for PCT/US2022/046384 dated Jan. 5, 2023.
Written Opinion for International Application No. PCT/US2022/024607 dated Oct. 12, 2023.

* cited by examiner

MONO DOSE DERMAL PATCH FOR PHARMACEUTICAL DELIVERY

TECHNICAL FIELD

The following relates to a dermal patch and more particularly to a dermal patch for delivering a pharmaceutical to a subject.

BACKGROUND

Typically, administration of a variety of pharmaceuticals, such as vaccines, is carried out via a multi-dose standard vial and syringe. In large majority, the delivery is intramuscular. This mode of administration requires the expertise of a medical professional, which can limit the availability of life-saving pharmaceuticals to certain patient populations. For example, in many developing areas of the world where access to medical professionals may be limited, such conventional modes of parenteral administration may deprive large segments of the population from access to needed pharmaceuticals.

Moreover, the multi-dose glass vial poses certain logistical and waste problems when used in large volumes for populations.

Furthermore, it has been found that intra-dermal or interstitial delivery of drugs including vaccines can have beneficial immunological effects as well as reduce the dose requirement. Fractional dosing is a key factor in creating affordability and in the case of pandemic response, rapid coverage of large patient volumes.

SUMMARY

Aspects of the present disclosure address the above-referenced problems and/or others.

In one aspect, a method for delivery of a pharmaceutical to a subject is disclosed, which includes applying a dermal patch to a subject's skin, wherein the dermal patch comprises a reservoir that stores a pharmaceutical and further comprises at least one hollow needle configured for puncturing the skin, actuating the at least one needle to puncture the subject's skin, and causing at least a portion of the stored pharmaceutical to be released from the reservoir for delivery via a lumen of the hollow needle to the subject.

In some embodiments, the dermal patch can further include a fluidic channel that is configured to deliver the pharmaceutical released from said reservoir to the lumen of said hollow needle.

In some embodiments, the dermal patch is configured to be a single-use patch. In some such embodiments, the reservoir contains a quantity of the pharmaceutical that is suitable for a single-dose administration to the subject.

A dermal patch according to the present teachings can be used to administer, i.e., intra-dermally or intra-muscularly, a variety of different pharmaceuticals. By way of example, in some cases, the pharmaceutical can be a vaccine, though other pharmaceuticals including a variety of inoculating formulations and therapeutic formulation, can also be administered via a dermal patch according to the teachings.

In some embodiments, the at least one needle can be an array of hollow needles. In some embodiment the needle can have a length in a range of about 100 microns to about 1600 microns.

In some embodiments, the dermal patch includes a reservoir that includes a compressible membrane and the step of causing the release of said stored pharmaceutical comprises applying pressure to said compressible membrane to cause at least a portion of the pharmaceutical to exit the reservoir.

The subject can be any of a human and an animal (i.e., pets, horses, cows, etc.).

In a related aspect, a dermal patch for delivering a pharmaceutical to a subject includes a frame, which includes a reservoir that contains a pharmaceutical and at least one hollow needle movable from a retracted position to an extended position such that, when in the extended position, the needle is configured to puncture the subject's skin to provide a passageway via a lumen thereof for delivery of at least a portion of the pharmaceutical stored in said reservoir to the subject, and at least one actuator for actuating the needle to move the needle between the retracted position and the extended position. The dermal patch includes an adhesive layer that is coupled to the frame for attaching the dermal patch to the subject's skin. In some embodiments, a protective liner can cover an adhesive surface of the adhesive layer. In use, the protective liner can be removed to expose the adhesive surface of the adhesive layer for attaching the dermal patch to a patient's skin.

In some embodiments of the above dermal patch, said at least one actuator is further configured to cause release of the pharmaceutical from the reservoir. In some embodiments, the at least one actuator comprises two actuators one of which is configured for activating said needle to move the needle from the retracted position to the extended position for puncturing the skin and another one of said actuators is configured to cause release of the pharmaceutical from the reservoir.

In some embodiments of the above dermal patch, the reservoir can include a compressible membrane and said at least one actuator can include a sliding mechanism operably coupled to said compressible membrane such that the sliding mechanism can be moved to compress said membrane for releasing the pharmaceutical from the reservoir for delivery to the subject.

In some embodiments of the above dermal patch, said at least one actuator can include a pump coupled to the reservoir, where the pump is actuable by a user to cause release of the pharmaceutical from the reservoir.

The reservoir of the dermal patch can be prefilled with a variety of different pharmaceuticals. In some such embodiments, the pharmaceutical is a vaccine. By way of example, the volume of the pharmaceutical stored in the reservoir can be, for example, in a range of about 0.5 mL to about 2 mL.

In some embodiments, said at least one needle is configured for intra-dermal administration of a pharmaceutical while in other embodiments, said at least one needle is configured for intra-muscular administration of a pharmaceutical. By way of example, the length of the needle can be adjusted to allow for intra-dermal or intra-muscular administration of a pharmaceutical on board the dermal patch, i.e., a pharmaceutical with which the reservoir of the dermal patch is prefilled.

In some embodiments, the dermal patch can include a needle cartridge to which said at least one needle (which typically includes an array of needles) is coupled. In some such embodiments, the dermal patch further includes a mount (i.e., a mount that can be releasably disposed into an enclosure provided by the frame) to which the needle cartridge can mounted. The actuator of the dermal patch can be operably coupled to the mount to cause its movement so as to transition the one or more needles coupled to the mount from a retracted position to an extended position in which the needle(s) can puncture a subject's skin. For example, the actuator can include an actuating element that is operably coupled to the mount for causing movement thereof.

In some such embodiments, the dermal patch can include a biasing element (i.e., a spring) that is coupled to the mount to facilitate activating the mount so as to move the needle cartridge from an undeployed (retracted) position to a deployed (expanded) position. In some such embodiment, the biasing element can be a spring that is maintained in a compressed state via a latch such that upon release of the latch, the spring expands and releases the potential energy stored therein to cause the movement of the mount and hence the needle cartridge that mounted onto the mount.

The frame can include an opening provided in a lower wall thereof through which the needle cartridge can pass, upon activation of the needle cartridge, so as to allow the needle(s) access the subject's skin and puncture the skin for delivery of the pharmaceutical to the subject.

In one aspect, a method for intra-dermal delivery of a pharmaceutical to a subject, includes applying a dermal patch to a subject's skin, wherein the dermal patch comprises a reservoir that stores a pharmaceutical and further comprises at least one hollow needle configured for puncturing the skin, actuating the at least one needle to puncture the subject's skin, and causing at least a portion of the stored pharmaceutical to be released from the reservoir for delivery via a lumen of the hollow needle to the subject.

In another aspect, a dermal patch for delivering a pharmaceutical to a subject includes a frame including a sealed reservoir that contains a pharmaceutical, and at least one hollow needle movable from a retracted position to an extended position such that, when in the extended position, the needle is configured to puncture the subject's skin and deliver at least a portion of the pharmaceutical via a lumen of the hollow needle to the subject and an adhesive layer coupled to the frame for attaching the dermal patch to the subject's skin.

In yet another aspect, a method includes applying a dermal patch containing a pharmaceutical to a subject and delivering the pharmaceutical to the subject via the dermal patch.

In yet another aspect, a dermal patch for delivering a pharmaceutical to a subject includes a frame to which a sealed reservoir that holds a pharmaceutical and an array of hollow needles are coupled. The dermal patch can include at least one actuator for actuating the needles to puncture a subject's skin and further cause the release of the pharmaceutical from the sealed reservoir for delivery to the subject via lumens of the hollow needles. An adhesive layer coupled to at least a portion of the bottom surface of the frame (i.e., the surface facing the skin upon application of the dermal patch to the subject's skin) can allow attaching the dermal patch to the subject's skin.

BRIEF DESCRIPTION OF THE DRAWINGS

Aspects of the present disclosure may take form in various components and arrangements of components, and in various steps and arrangements of steps. The drawings are only for illustration purpose of preferred embodiments of the present disclosure and are not to be considered as limiting.

Features of embodiments of the present disclosure will be more readily understood from the following detailed description take in conjunction with the accompanying drawings in which.

DETAILED DESCRIPTION

Figure 1:
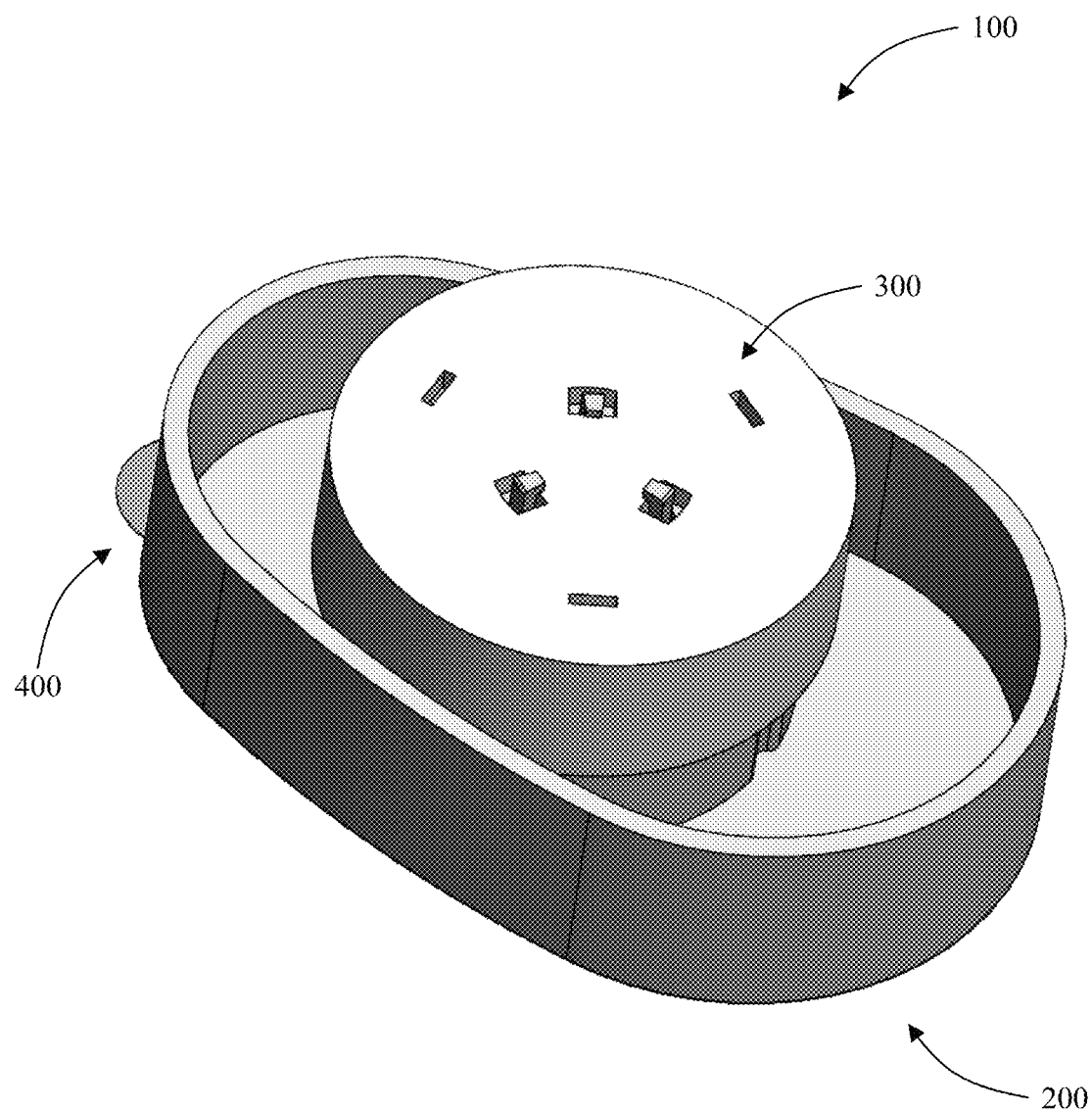
FIG. 1 depicts a dermal patch in accordance with an exemplary embodiment.
Figure 2:
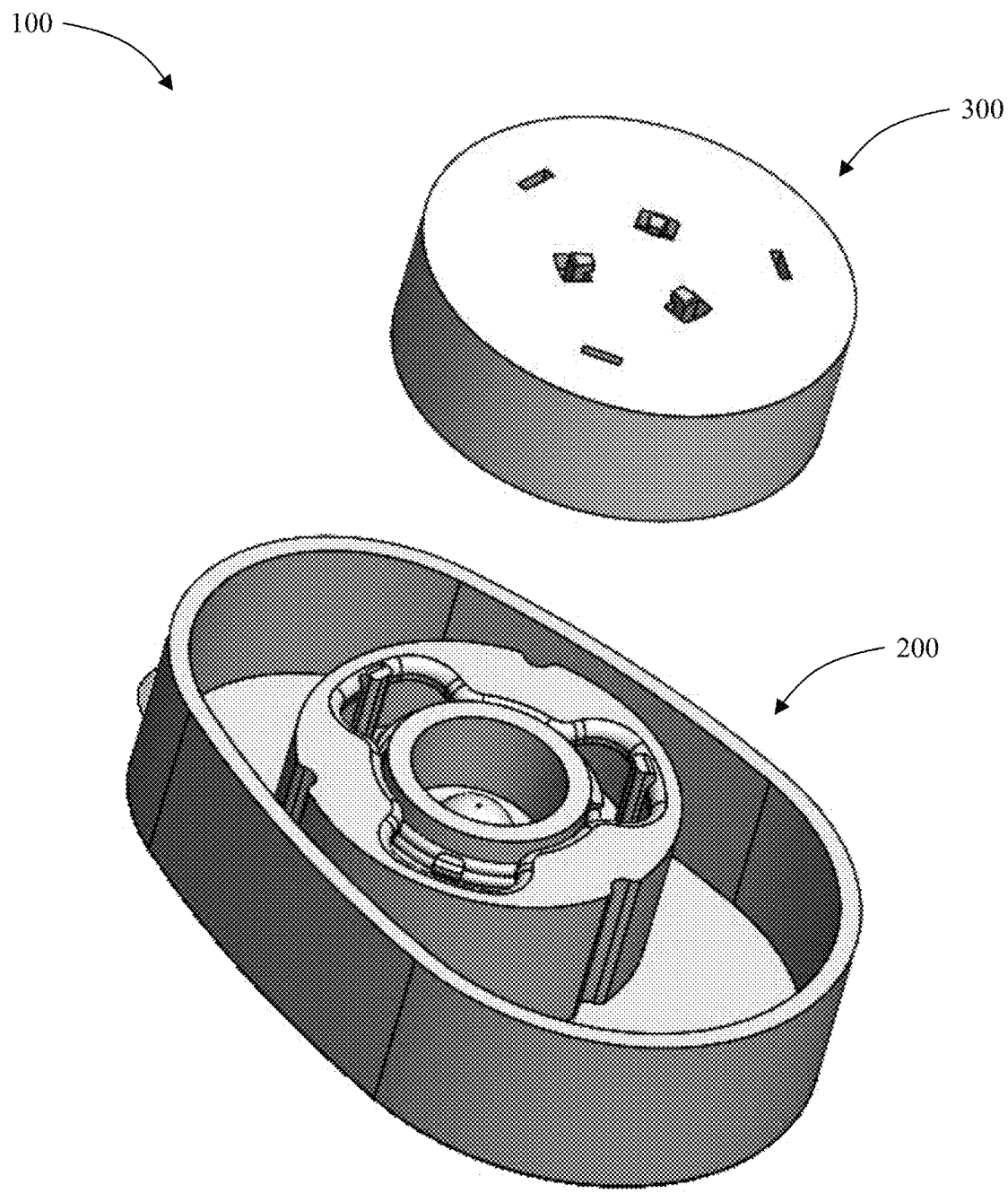
FIG. 2 depicts a dermal patch with an actuator removed from a frame of the dermal patch in accordance with an exemplary embodiment.

The present disclosure generally relates to a dermal patch for delivering a pharmaceutical (i.e., vaccines, medications, etc.) to a subject.

Some embodiments of the present disclosure include a dermal patch prefilled with a predetermined amount of a pharmaceutical for intradermal administration to a subject. As discussed in more detail below, in embodiments, such a dermal patch may include a reservoir in which a quantity of a pharmaceutical is stored. The dermal patch can also include a pharmaceutical delivery element for the administration of the pharmaceutical on board the dermal patch to a subject. In use, the dermal patch can be applied to the skin of a subject and the pharmaceutical delivery element can be actuated to puncture the skin to allow delivery of the pharmaceutical to the subject. As discussed in more detail below, in some such embodiments, the pharmaceutical delivery element can also cause release of the pharmaceutical from the reservoir in which the pharmaceutical is stored. In some other embodiments, the dermal patch can include a separate release element for causing the pharmaceutical to exit the reservoir and be delivered to the subject.

A dermal patch that delivers a predetermined quantity of a pharmaceutical to a subject can provide a number of advantages. For example, it can allow for the delivery of a pharmaceutical without a need for a highly trained medical professional. Further, it can allow for the delivery of a more accurate dose of a pharmaceutical to a subject, as the on-board pharmaceutical reservoir may be prefilled with a dose of the pharmaceutical more accurately than a standard syringe.

Further embodiments of the present disclosure include a dermal patch with retractable needles that deliver a pharmaceutical. Providing a dermal patch with retractable needles increases the safety of the dermal patch as the needles may only be exposed to an environment external to the dermal patch when delivering the pharmaceutical.

In some embodiments, the dermal patch is a single-use dermal patch. Stated another way, the dermal patch can be preconfigured to contain a single dose of a pharmaceutical and cannot be refilled after administration of the pharmaceutical to the subject. Providing a single-use dermal patch for administering a pharmaceutical, such as a vaccine, can reduce the risk of contamination between subjects.

Furthermore, the dermal patch can deliver the pharmaceutical intradermally. Providing a dermal patch that can deliver a pharmaceutical intradermally may reduce the cost of administering the pharmaceutical as less pharmaceutical may be needed (i.e., a fractional dose) when compared with standard intramuscular delivery systems (i.e., a vial and syringe system).

The terms "needle" and "microneedle" are used herein to broadly refer to an element that can provide a passageway, or facilitate the production of a passageway, for administering a pharmaceutical (i.e., vaccine, medication, etc.) through a subject's skin (i.e., by puncturing the subject's skin.

The terms "pharmaceutical" and "pharmaceutical formulation" as used herein refers to any formulation used in the treatment of a medical condition. Pharmaceuticals include, but are not limited to, vaccines (i.e., bacterial vaccines, viral vaccines, mRNA vaccines, etc.) and medications that may be delivered via an injection.

The term "subject" as used herein refers to a human subject or an animal subject (i.e., chicken, pig, cattle, dog, cat, etc.).

As used herein, the term "about" means plus or minus 10% of the numerical value of the number with which it is being used. Therefore, about 100 μm means in the range of 90 μm-110 μm.

As used herein a "longitudinal" direction is a direction that is substantially orthogonal to a bottom wall of a frame a dermal patch.

As used herein, a "horizontal" direction is a direction that is substantially parallel to a bottom wall of a frame of a dermal patch.

While the following describes a dermal patch for intradermal administration of a pharmaceutical to a subject, in other embodiments, the dermal patch may be modified by changing the needles of the dermal patch (i.e., by providing a dermal patch with longer needles) such that the dermal patch is capable of delivering a pharmaceutical to a subject via an intramuscular injection.

Referring now to FIGS. 1-17 a dermal patch 100 is shown in accordance with an exemplary embodiment. The dermal patch includes a frame 200 and an actuator 300.

Referring now to FIGS. 1-17, a dermal patch 100 includes a frame 200 and an actuator 300, which can be removably coupled to the frame 200, while in other embodiments the actuator 300 can be integrally affixed to the frame 200. As discussed in more detail below, the actuator 300 can be coupled to the frame 200 to actuate an array of hollow needles coupled to the frame to puncture the subject's skin. In some embodiments, the same or a different actuator can also cause the release of at least a portion of the pharmaceutical stored in a sealed reservoir to allow the delivery thereof via lumens within the hollow needles to the subject.

The frame 200 includes a bottom wall 202 having an inner surface 202a and an outer surface 202b opposite the inner surface 202a, which faces a subject's skin upon application of the dermal patch to the subject's skin. The bottom wall 202 defines an aperture 204 that extends between the inner surface 202a and the outer surface 202b and through which an array of hollow needles can pass, when actuated, to puncture the skin and allow the administration of the pharmaceutical on board the patch via the lumens of the hollow needles through the skin punctured by those needles.

Figure 4:
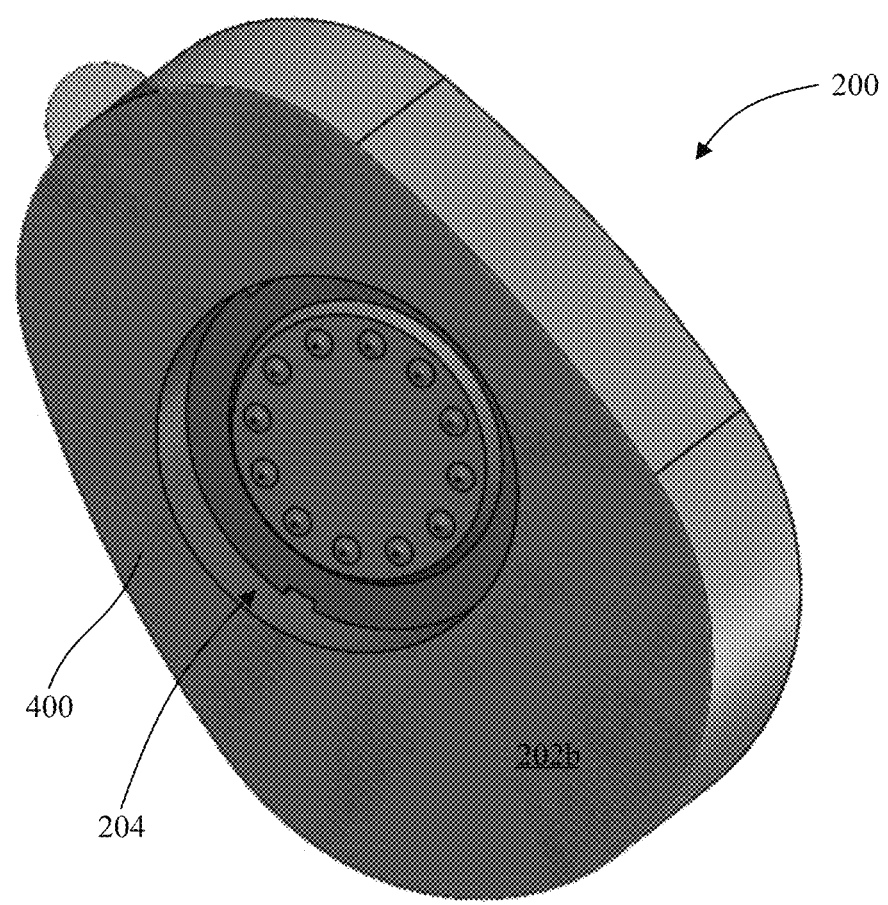
FIG. 4 depicts a bottom side of a dermal patch in accordance with an exemplary embodiment.

With particular reference to FIG. 4, the dermal patch 100 further includes an adhesive layer 400 disposed on the outer surface 202b of the frame 200 so as to surround the aperture 204, where the adhesive layer allows attaching the dermal patch to a subject's skin. In some embodiments, a protective liner (not shown in the figures) can cover the adhesive layer, where the protective liner can be removed prior to attachment of the dermal patch to the subject's skin for exposing the adhesive surface of the adhesive layer. More specifically, in use, the dermal patch 100 may be attached to a subject's skin via the adhesive layer 400 by removing the protective liner so as to expose the adhesive layer for attachment of the dermal patch to the skin, i.e., to a subject's arm or leg or any other portions of the subject.

The frame 200 further includes a peripheral wall 206 that extends longitudinally from and perpendicular to the bottom wall 202. The peripheral wall 206 includes an inner surface 206a and an outer surface 206b opposite the inner surface 206b. The peripheral wall 206 further includes a top surface 206c, which extends horizontally between the inner surface 206a and the outer surface 206b.

Figure 3:
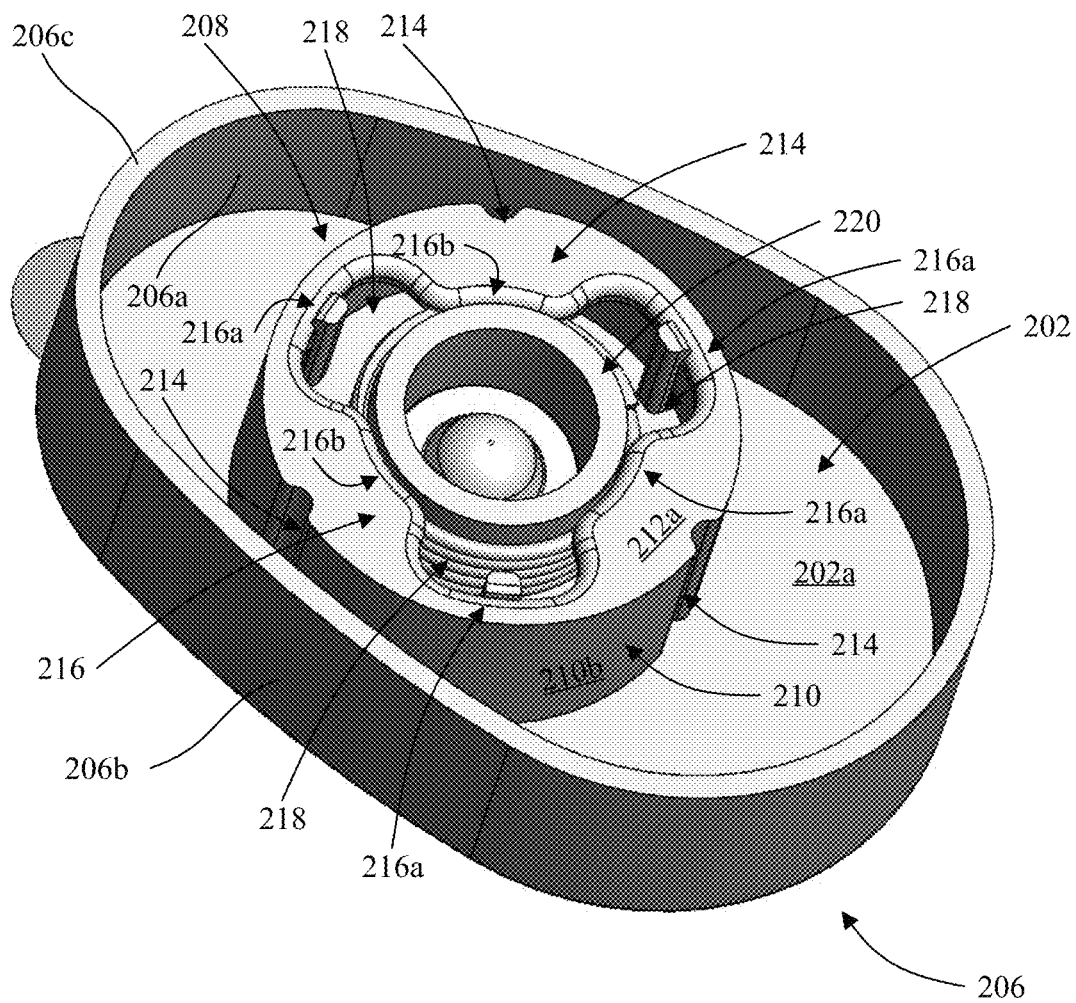
FIG. 3 depicts a frame of a dermal patch in accordance with an exemplary embodiment.

With particular reference to FIG. 3, the frame 200 further includes an enclosure 208 formed by an inner wall 210 that extends longitudinally from and perpendicular to the bottom wall 202 and a top wall 212 that extends between opposing sides of the inner wall 210. The enclosure 208 is configured for receiving a mount 500 to which an array of needles can be mounted.

The inner wall 210 includes an inner surface 210a and a substantially cylindrical outer surface 210b opposite the inner surface 210a. While the inner wall 210 is depicted as being cylindrical, in other embodiments the inner wall 210 may have a different shape. The inner wall 210 further includes a plurality of vertical grooves 214 that are formed in the outer surface 210b. The grooves 214 extend longitudinally from the bottom wall 202 to the top wall 212.

The top wall 212 includes a top surface 212a and a bottom surface 212b opposite the top surface 212a. A curved rim 216 extends between the top surface 212a and the bottom surface 212b. The curved rim 216 includes a plurality of sections 216a that are separated by a plurality of segments 216b of the curved rim 216. The sections 216a define a plurality of recesses 218 and the segments 216b define an opening 220. The opening 220 is shaped and dimensioned to accommodate a mount to which an array of hollow needles is mounted, as discussed in more detail below. Further, as discussed in more detail below, the mount can include a plurality of latches that can engage with the sections 216a of the curved rim 216. The inner surface 210a of the inner wall 210 and the bottom surface 212b of the top wall 212 define an inner volume 222 of the frame 200. As will be discussed in further detailed herein the inner volume 222 is shaped and dimensioned to accommodate the mount with the needle array. While the top wall 212 is depicted as an element of the frame 200, in other embodiments, the top wall 212 may be part of the actuator 300. Furthermore, the top wall 212 may be moveable and may be detached from the frame 200.

Figure 5:
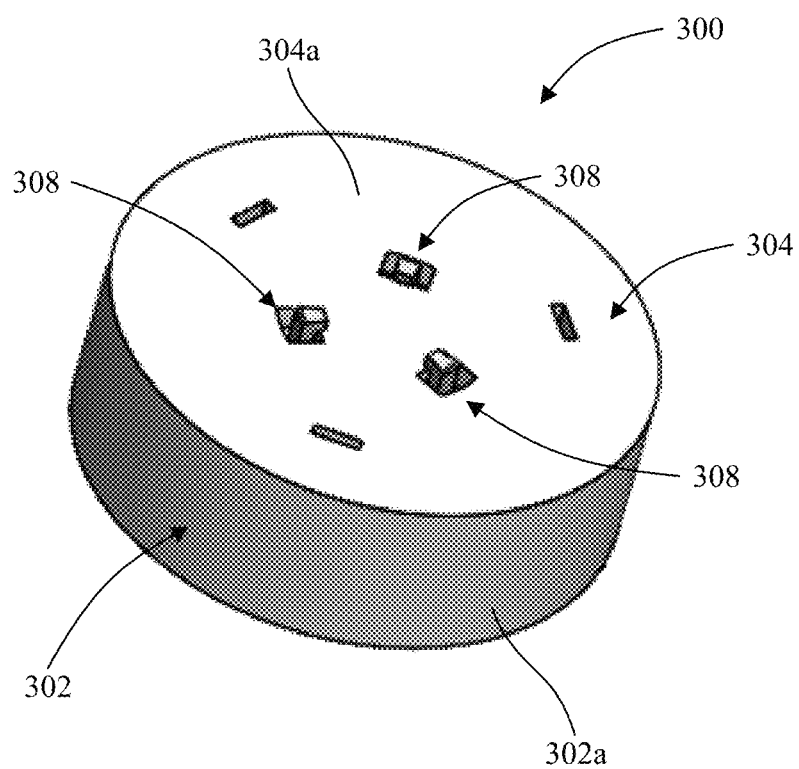
FIG. 5 depicts an actuator of a dermal patch in accordance with an exemplary embodiment.
Figure 6:
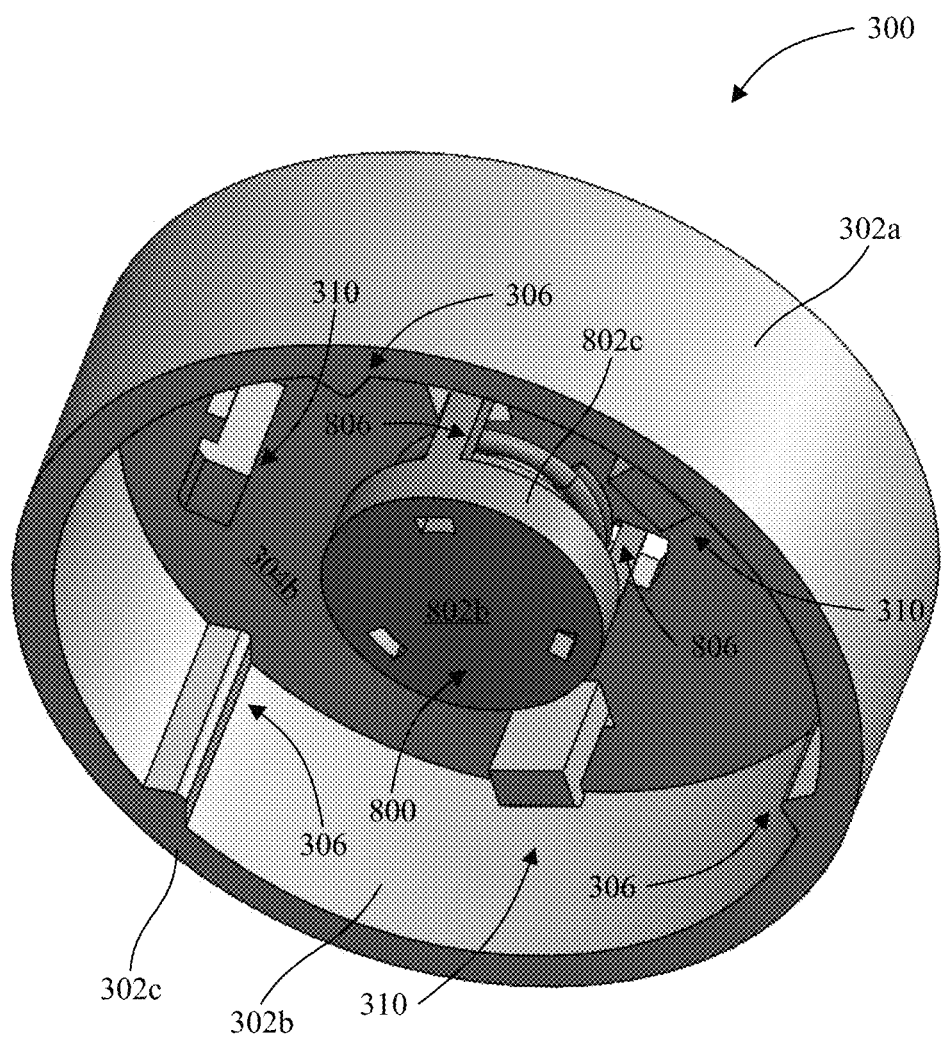
FIG. 6 depicts a bottom side of an actuator of a dermal patch in accordance with an exemplary embodiment.

With particular reference to FIGS. 5 and 6, the actuator 300 includes a peripheral wall 302, which is substantially cylindrical, and a top wall 304 having an outer surface 304a and an inner surface 304b. The peripheral wall 302 extends longitudinally from and perpendicular to the top wall 304. The peripheral wall 302 includes an outer surface 302a and an opposed inner surface 302b opposite the inner surface and a bottom surface 302c, which extends between and perpendicular to the outer surface 302a and the inner surface 302b. The peripheral wall 302 further includes a plurality of protrusions 306 that are defined by the inner surface 302b. The protrusions 306 extend longitudinally from the inner surface 304a of the top wall 304 to the bottom surface 302c of the peripheral wall 302. The top wall 304 defines a plurality of openings 308. As will be discussed in further detail herein, the openings 308 are shaped and dimensioned to accommodate a latch of the mount.

As depicted in FIG. 1, the actuator 300 is shaped such that the peripheral wall 302 thereof fits circumferentially around inner wall 210 of the frame 200. When the actuator 300 is placed over the inner wall 210, the protrusions 306 of the actuator 300 slide within the grooves 214 of the frame 200. As will be discussed in further detail herein, the actuator 300 is moveable. When moved, the grooves 214 and the protrusions 306 guide the movement of the actuator 300. While the dermal patch 100 is described as having grooves 214 and protrusions 306, in other embodiments other shaped elements may be used to guide the actuator (i.e., a divet or a dimple).

The actuator 300 further includes a plurality of latches 310. The latches 310 extend longitudinally from and perpendicular to the bottom surface 304b of the top wall 304.

Figure 7:
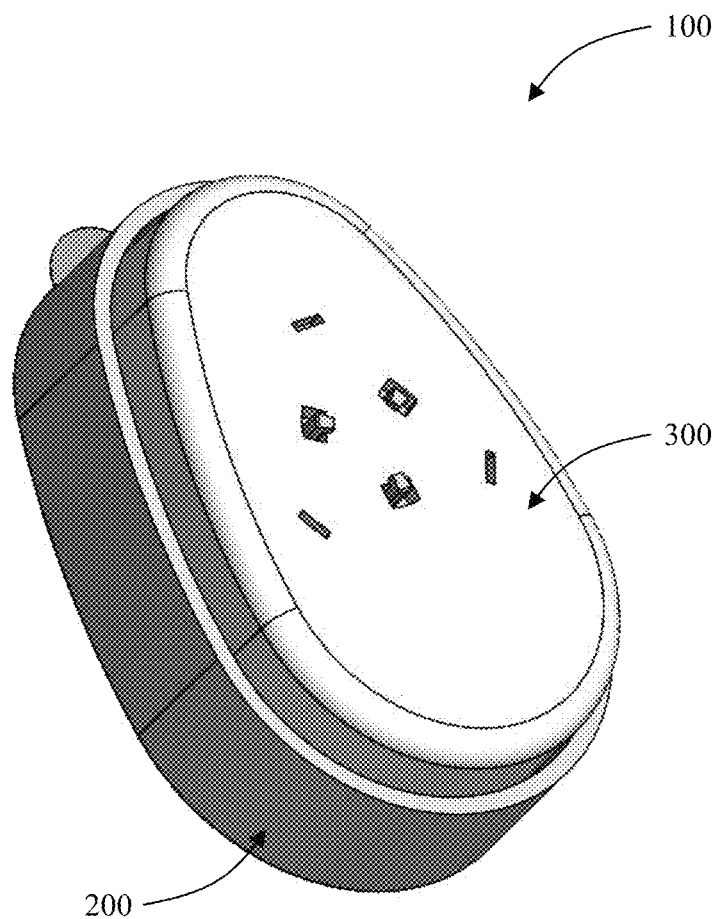
FIG. 7 depicts another embodiment of a dermal patch in accordance with an exemplary embodiment.
Figure 8:
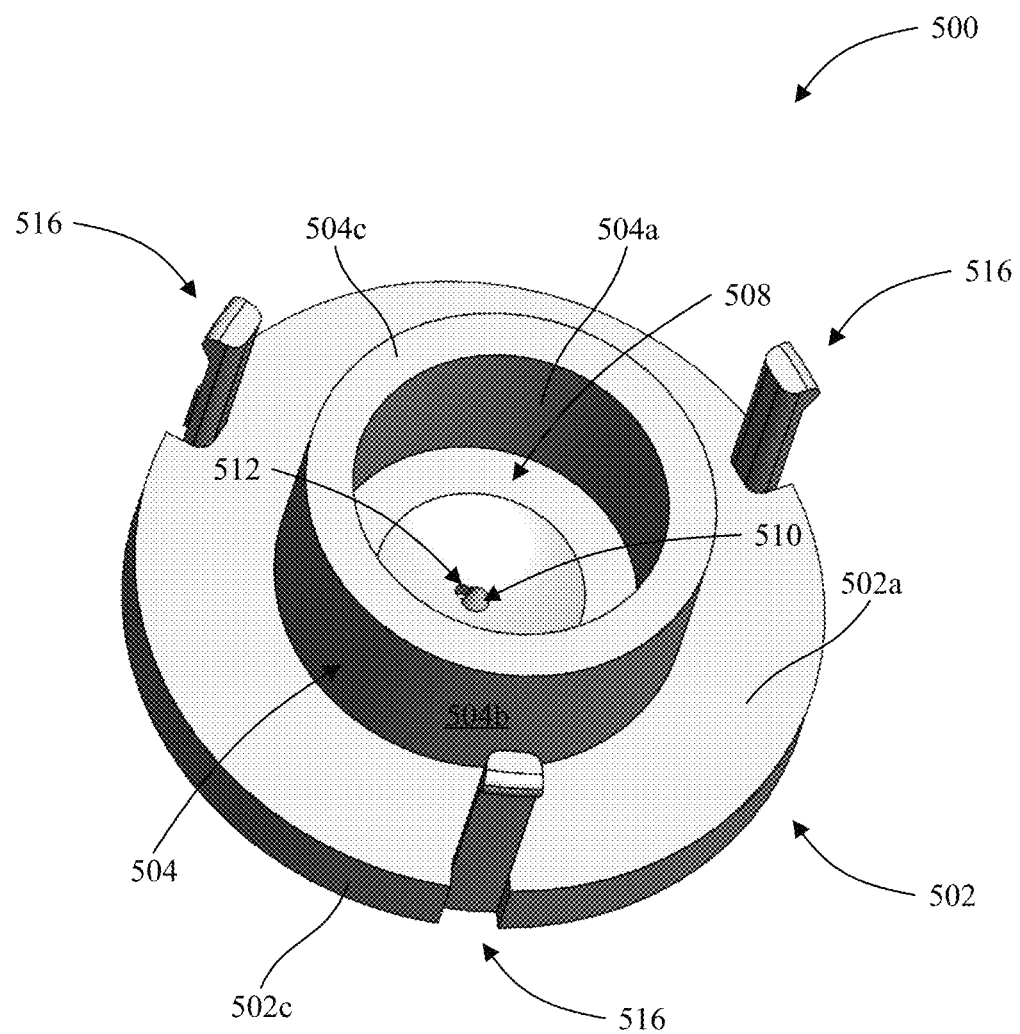
FIG. 8 depicts a mount of a dermal patch in accordance with an exemplary embodiment.
Figure 9:
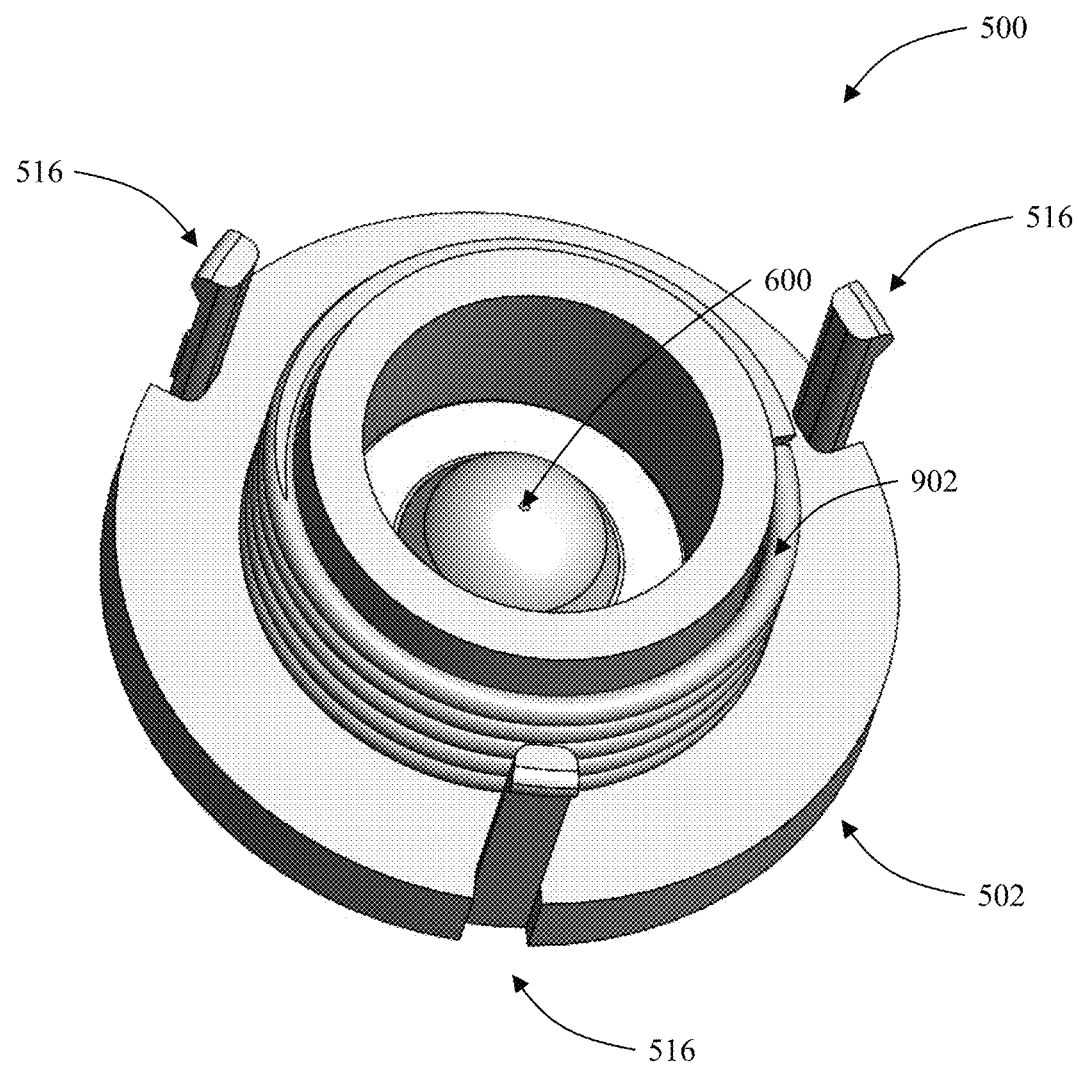
FIG. 9 depicts a mount and a sealed reservoir of a dermal patch in accordance with an exemplary embodiment.
Figure 10:
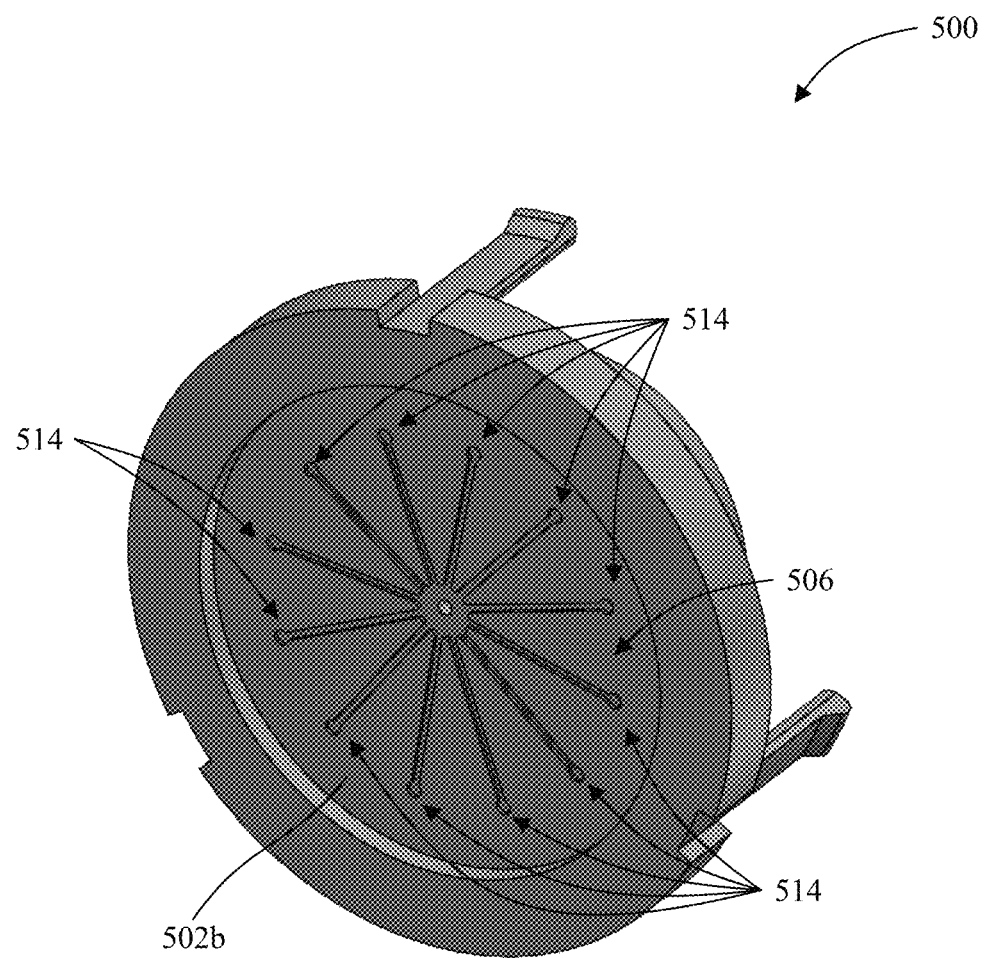
FIG. 10 depicts a bottom of a mount in accordance with an exemplary embodiment.
Figure 11:
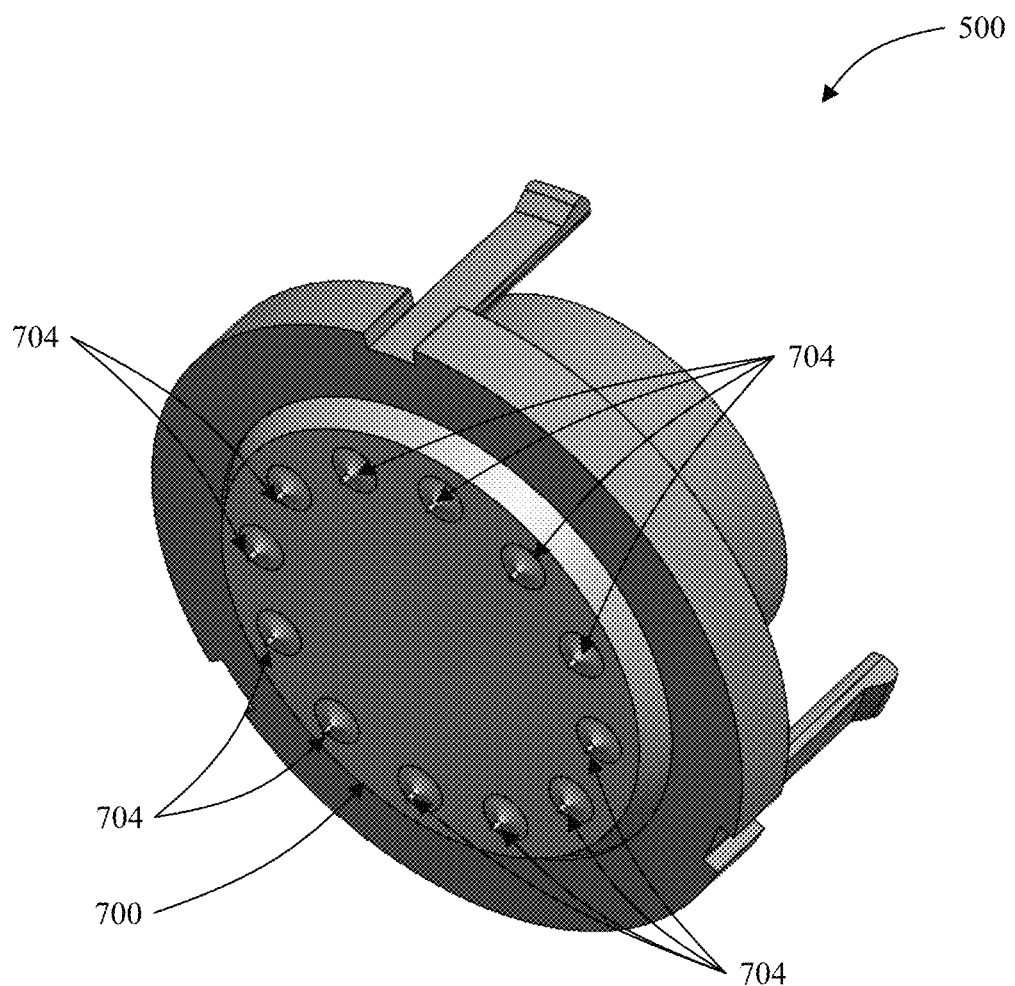
FIG. 11 depicts a mount and a pharmaceutical-delivery cartridge in accordance with an exemplary embodiment.

While FIGS. 5 and 6 depict the actuator 300 as having a cylindrical shape, in other embodiments the actuator 300 may have a different shape. For example, as depicted in FIG. 7, in another embodiment, the actuator 300 may have substantially the same profile as the frame 200.

The dermal patch 100 further includes a mount 500 that can be releasably placed in the enclosure 208. The mount 500 includes a bottom wall 502 and a peripheral wall 504 that extends longitudinally from and perpendicular to the bottom wall 502.

The bottom wall 502 includes a top surface 502a, a bottom surface 502b opposite the top surface 502a, and an outer surface 502c that extends longitudinally between and perpendicular to the top surface 502a and the bottom surface 502b. The outer surface 502c is cylindrical in shape and contacts the inner surface 210a of the inner wall 210 when the mount 500 is installed within the enclosure 208. Stated another way, the bottom wall 502 is shaped such that the mount 500 fits within the inner volume 222. The bottom wall 502 forms a recess 506 which is configured to receive a needle cartridge 700 that includes a plurality of hollow needles 704. While the needle cartridge 700 is depicted as being circular, in other embodiments the needle cartridge may have a different shape.

The peripheral wall 504 includes an inner surface 504a, an outer surface 504b opposite the inner surface, and a top surface 504c that extends between the inner surface 504a and the outer surface 504b. The inner surface 504a defines an inner volume 508.

The mount 500 further includes a piercing element 510. While mount 500 is depicted as including one piercing element 510, in other embodiments the mount 510 may include a plurality of piercing elements 510. The piercing element 510 extends longitudinally from the bottom wall 502. The piercing element 510 includes a sharp point that aids in delivering a pharmaceutical to a subject. The mount 500 includes an opening 512 that is in fluid communication with a plurality of microfluidic channels 514 that are formed in the bottom surface 502b of the bottom wall 502 and extend radially from the opening 512 to connect to lumens of a plurality of hollow needles when needles are mounted onto the mount 500. The microfluidic channels 514 may have a depth of 200 to 500 microns.

The mount 500 further includes a plurality of latches 516 that extend longitudinally from and perpendicular to the base bottom wall 502, which can engage with the sections 216a of the curved rim 216.

The dermal patch 100 further includes a sealed reservoir 600 that is prefilled with a pharmaceutical. In one embodiment the reservoir 600 is in the form of a blister pack. In another embodiment, the reservoir 600 is a blow-fill-sealed reservoir. The reservoir 600 is dimensioned and shaped to fit within the inner volume 508 of the mount 500. The reservoir 600 is sealed by a frangible membrane 602 and retains a quantity of a pharmaceutical In some embodiments, the reservoir 600 is pre-filled with a predetermined quantity of a pharmaceutical that is sufficient for the administration of a single dose of the pharmaceutical to the subject.

The dermal patch 100 further includes a needle cartridge 700. In this embodiment, the needle cartridge 700 can be received in the recess 506 of the mount.

In this embodiment, the needle cartridge 700 includes a platform 702 to which a plurality of needles 704 is coupled. The platform 702 is shaped as a disk having a top surface 702a, an opposed bottom surface 702b, and a peripheral surface 702c that extends longitudinally between the top surface 702a and the bottom surface 702b. When coupled to the mount 500, the top surface 702a of the platform 702 couples to the bottom surface 502b of the bottom wall 502.

Once the needle cartridge is coupled to the mount 500, the upper surface of the cartridge and the microfluidic channels formed in the lower surface of the mount 500 form fluidic passages through which the pharmaceutical released from the reservoir 600 can be delivered to the lumen of hollow needles 704 for delivery to a subject.

The hollow needles 704 are configured to puncture the skin of a subject and deliver a pharmaceutical to the subject. While the dermal patch 100 is depicted as including 12 needles, in other embodiments, the dermal patch may include a different number of needles (i.e., 1, 7, 15, 20, etc.). Furthermore, while the needles 704 are depicted as arranged in a circular pattern around the circumference of the platform 702, in other embodiments the needles 704 may be arranged in a different pattern (i.e., in a linear pattern, in a checkerboard pattern, in a semi-circular pattern, etc.).

In some embodiments, the needles 704 are microneedles are about 100 microns to about 1600 microns in length, about 50 to about 250 microns in width, and about 1-25 microns in diameter, though other sizes may also be employed. For example, when the dermal patch is configured for intradermal administration of a pharmaceutical, the needles can have a length in a range of about 100 microns to about 800 microns. In other embodiments in which the needles are configured for intramuscular administration of a pharmaceutical, the needles can have a length in a range of about 800 microns to 1600 microns, though any other suitable lengths for intra-dermal or intra-muscular administration can also be employed.

The bottom wall 502 and therefore the needle cartridge 700 is in register with the aperture 204 of the frame 200. As will be discussed in further detail herein, the mount 500 is moveable such that the needle cartridge 700 extends through the aperture 204.

The dermal patch 500 further includes a pin 800. The pin 800 includes a base 802, an outer wall 804. The base 802 includes a top surface 802a, a bottom surface 802b opposite the top surface 802a, and an outer surface 804c that extends longitudinally between and perpendicular to the top surface 802a and the bottom surface 802b. The outer surface 802c is cylindrical in shape and contacts the inner surface 504a of the peripheral wall 504 when the pin 800 is installed within the mount 500. Stated another way, the base 802 is shaped such that the pin 800 fits within the inner volume 508 of mount 500.

The outer wall 804 extends longitudinally from and perpendicular to the base 802. The outer wall 804 and the base 802 have the same circumference. The outer wall 804 has an inner surface 804a and an outer surface 804b. When the pin 800 is installed in the mount 500, the outer surface 804b contacts the inner surface 504a of the peripheral wall 504.

The pin 800 further includes a plurality of latches 806. The plurality of latches 806 extend longitudinally from and perpendicular to the base 802.

The dermal patch 100 further includes a first biasing element (or a first spring) 902 and a second biasing element (or a second spring) 904.

The first biasing element 902 biasing element is disposed circumferentially about the inner wall 210 of the enclosure 208. The first biasing element includes a top end 902a and an opposed bottom end 902b. The top end 902a contacts the bottom surface 212b of the top wall 212 of the frame 200 and the bottom end 902b contacts the top surface 502a of the bottom wall 502 of the mount 500. Stated another way, the first biasing element 902 extends longitudinally between the bottom surface 212b of the top wall 212 and the top surface 502a of the bottom wall 502.

The second biasing element 904 extends horizontally between opposing sides of the inner surface 804a of the outer wall 804 and between latches 806 of the pin 800. The inner surface 804a and the latches 806 retain the second biasing element 904. The second biasing element 904 includes a top end 904a and a bottom end 904b. The top end 904a contacts the bottom surface 304b of the top wall 304 of the actuator 300. The bottom end 904b contacts the top surface 802a of the base 802 of the pin 800.

Figure 12:
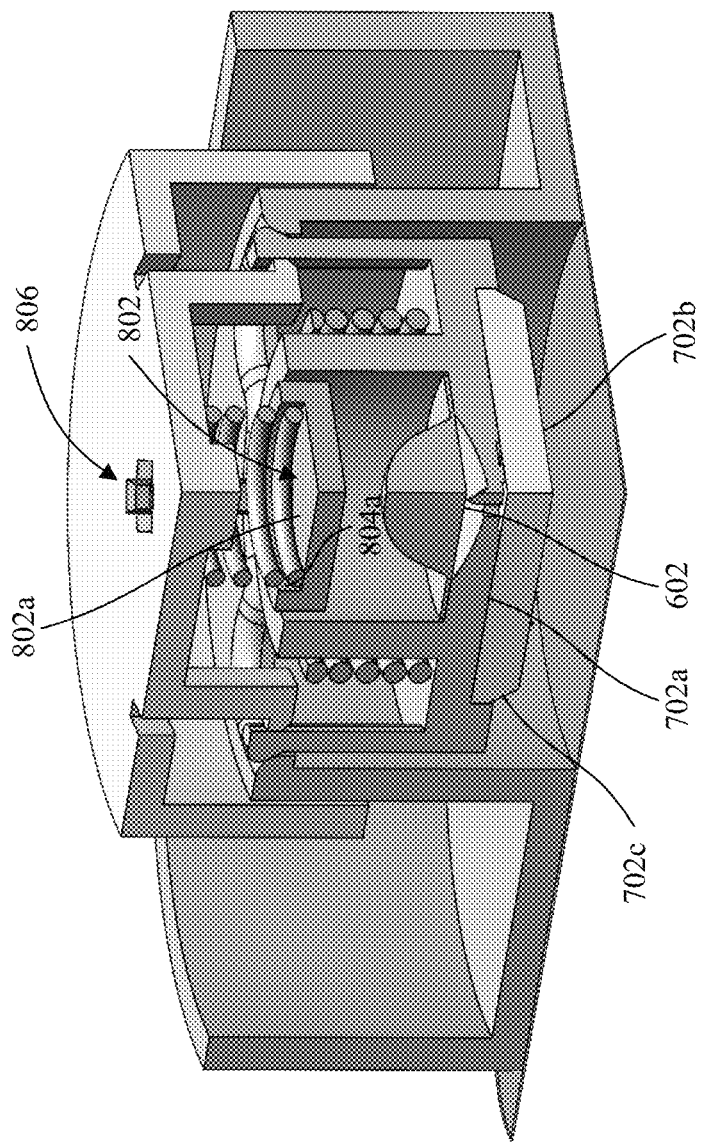
FIG. 12 is a cross-sectional view of a dermal patch in an undeployed position in accordance with an exemplary embodiment.

In use, the dermal patch 100 can be adhered to the skin of a subject via the adhesive layer 400. Once the dermal patch 100 has been applied to a subject's skin, the dermal patch 100 may be used to deliver a pharmaceutical to the subject. Initially, as depicted in FIG. 12, the dermal patch 100 is in an undeployed position in which the mount 500 is fully disposed within the inner volume 222 of the frame 200 and the needle cartridge 700 and hence the needles 704 are fully retracted within the inner volume 222.

In the retracted position, the needles 702 are not able to puncture skin of the subject. In the undeployed position the first biasing element 902 is in a compressed state relative to its natural state. In this state, the first biasing element 902 has an elastic potential energy as a result of this deformation.

The latches 516 of the mount 500 and the latches 310 of the actuator 300 and retain the mount 500 in the undeployed position. In the undeployed position, the ends of the latches 310 extend through the opening 508 of the frame 200 and press the ends of the latches 516 into the top wall 212 such that the ends of the latches 516 hook to the top surface 212a of the top wall 212 of the frame 200. This force is greater than the elastic potential energy of the first biasing element 902 thereby preventing the first biasing element 902 from expanding and moving the mount 500.

Figure 13:
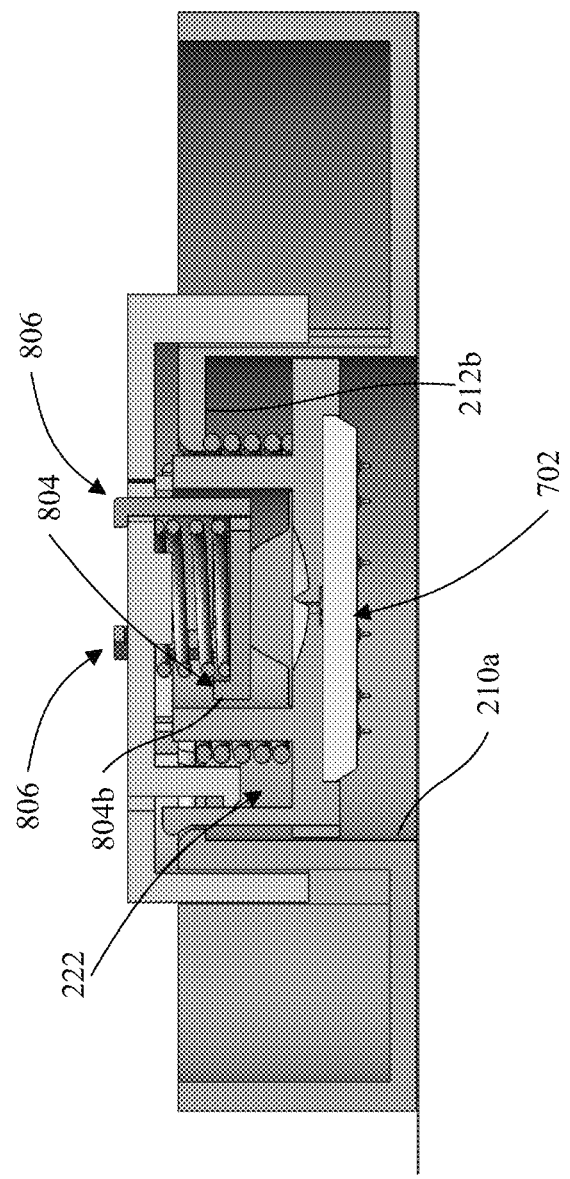
FIG. 13 is a cross-sectional view of a dermal patch wherein an actuator of the dermal patch is in a deployed needle position in accordance with an exemplary embodiment.
Figure 14A:
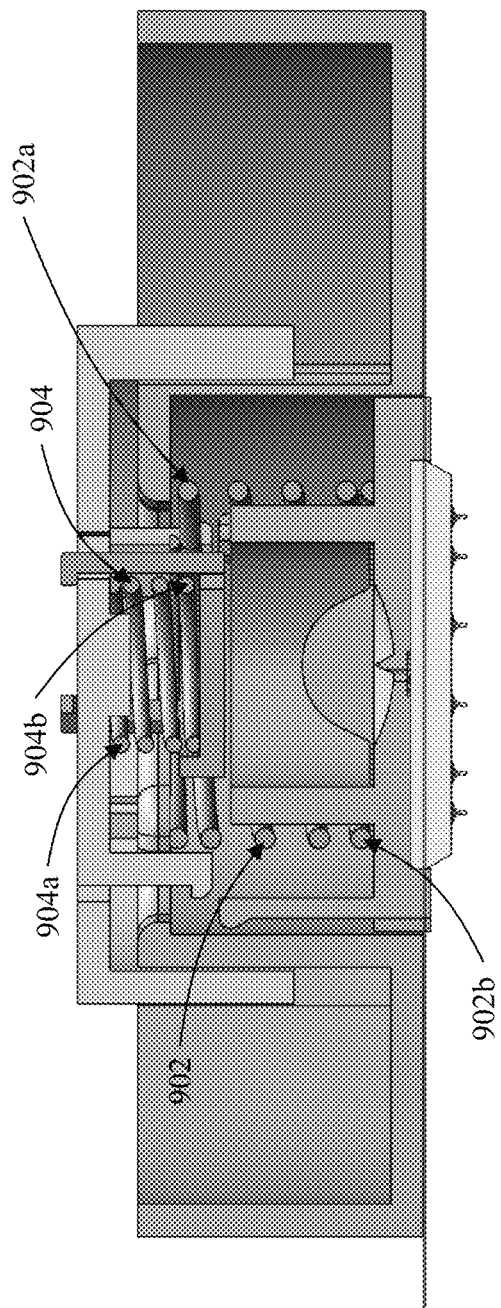
FIG. 14A is a cross-sectional view of a dermal patch wherein needles of the dermal patch are in an extended position in accordance with an exemplary embodiment.
Figure 14B:
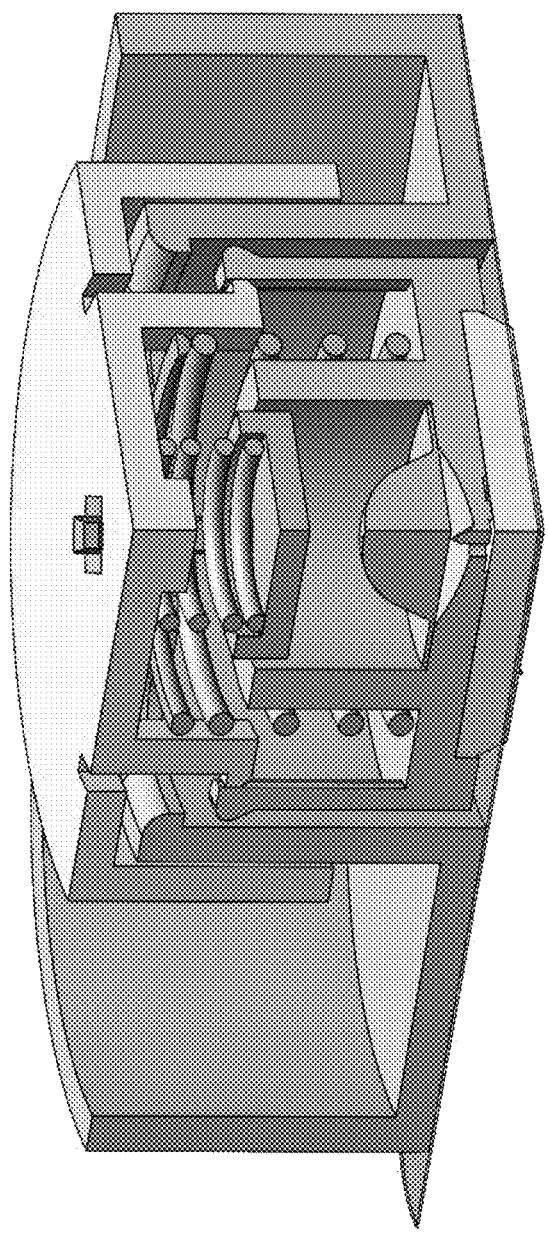
FIG. 14B is another cross-sectional view of a dermal patch wherein needles of the dermal patch are in an extended position in accordance with an exemplary embodiment.

As depicted in FIG. 13 the actuator 300 may be pressed a first time with a first force to move the actuator 300 to a deployed needle position. When moving the actuator 300 into the deployed needle position, the grooves 306 serve as a guide for the actuator 300. That is, the protrusions 214 slide within the grooves 306 such that a horizontal position of the actuator 300 is maintained while the actuator 300 is moved in a vertical direction. In the deployed needle position, the latches 310 of the actuator 300 no longer press the ends of the latches 516 into the top wall 212 of the frame 200 (FIG. 13). When the latches 516 are no longer pressed into the top wall 212, the latches 516 are able to release from the top wall 212 and when the latches 516 are released, the first biasing element 904 is able to expand thereby moving the mount 500 into a deployed position (FIGS. 14A and 14B). Stated another way, the top end 902a of the first biasing element 902 pushes against the bottom surface 212b of the top wall 212 and the bottom end 902b of the first biasing element 902 pushes against the top surface 502a of the bottom wall 502. Since the mount 500 is moveable and the top wall 212 is not, this force moves the mount 500 to the deployed position. When the mount 500 is in the deployed position, the needle cartridge 700 and the needles 702 extend through the aperture 204 of the frame 200. In this position, when the dermal patch 100 is adhered to skin of a subject, the needles 702 puncture the skin and enter the epidermis of the subject.

Figure 16:
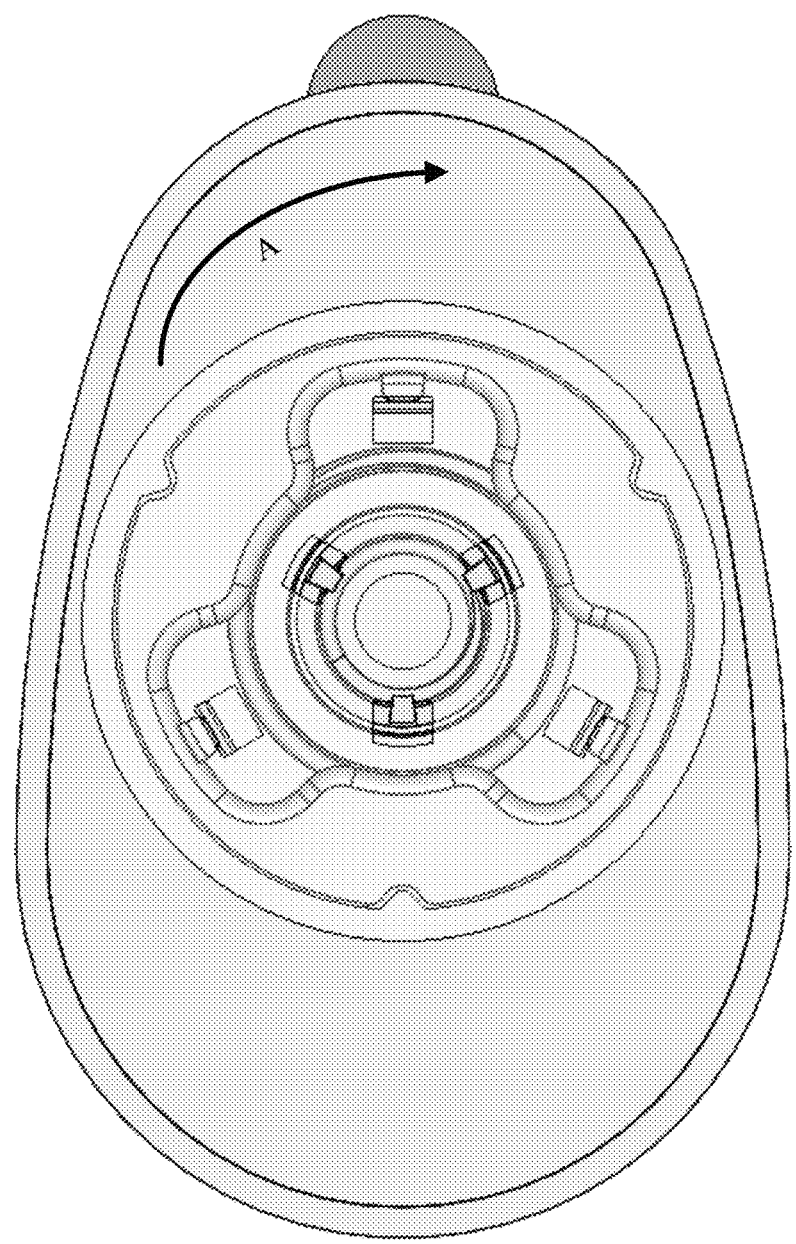
FIG. 16 is a top view of a dermal patch in accordance with an exemplary embodiment.
Figure 17:
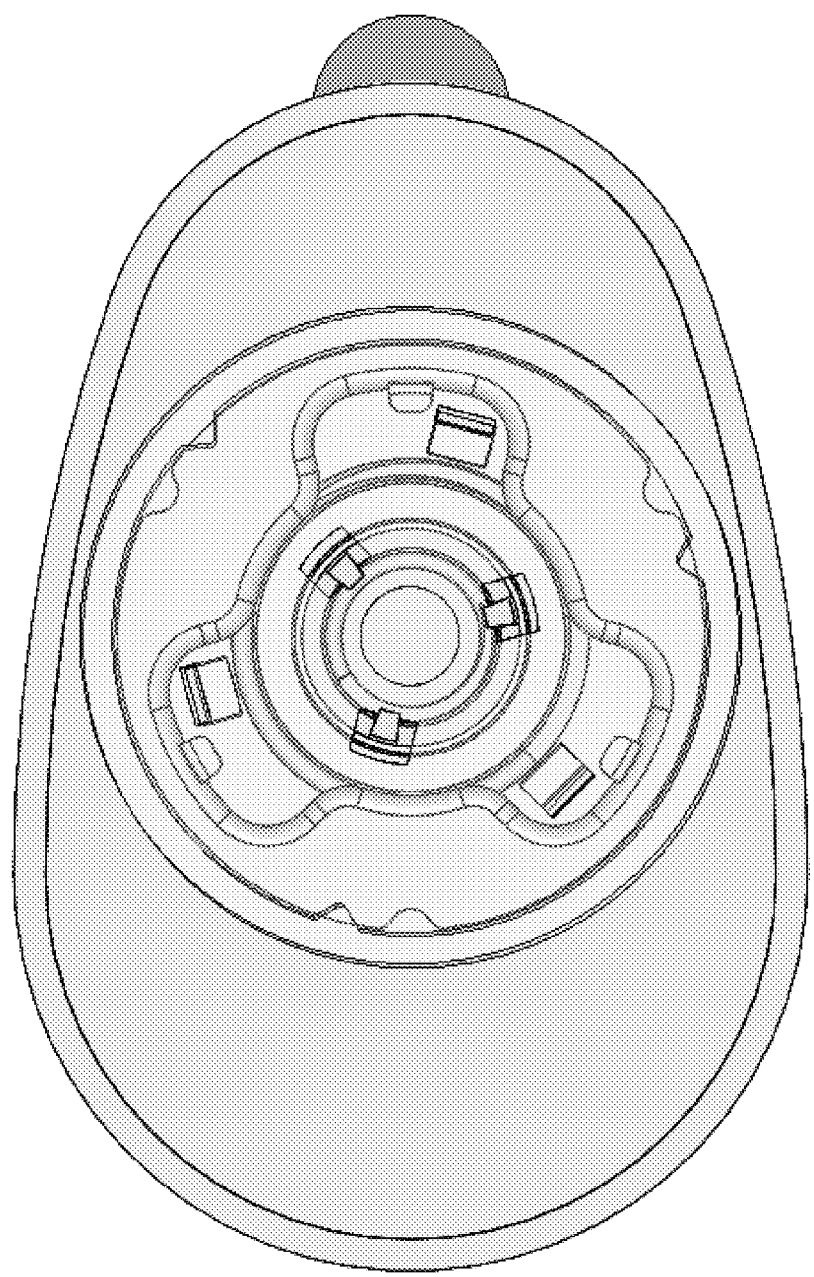
FIG. 17 is a top view of a dermal patch wherein an actuator of the dermal patch has been rotated in accordance with an exemplary embodiment.

While FIGS. 12-14 depict the actuator 300 as moving in a vertical direction in order to move into the deployed needle position, in another embodiment, the actuator 300 may be rotated into the deployed needle position. For example, as depicted in FIG. 16 the actuator may be rotated in the direction of arrow A. When rotated the latches 516 are able to release from the top wall 212 which allows the first biasing element 902 to move the mount 500 into the deployed position as previously discussed herein and as depicted in FIG. 17. In this embodiment, the grooves 214 and the protrusions 306 are parallel to the bottom wall 202 such that the grooves 214 rotationally guide the movement of the actuator 300.

When the actuator 300 is in the undeployed position and the deployed needle position, the pin 800 is in an undeployed position. In this position, the pin 800 is not able to contact the reservoir 600. In the undeployed position the second biasing element 904 is in a compressed state relative to its natural state. In this state, the second biasing element 904 has an elastic potential energy as a result of this deformation. The latches 806 of the pin 800 retain the pin 800 in the undeployed position. In the undeployed position, ends of the latches 806 extend through the openings 308 and hook to the top surface 304a of the top wall 304 of the actuator 300. A component of the actuator 300 presses the latches 800 into the top wall 304 with a force that is greater than the elastic potential energy of the second biasing element 904 thereby preventing the second biasing element from expanding and moving the pin 800.

Figure 15:
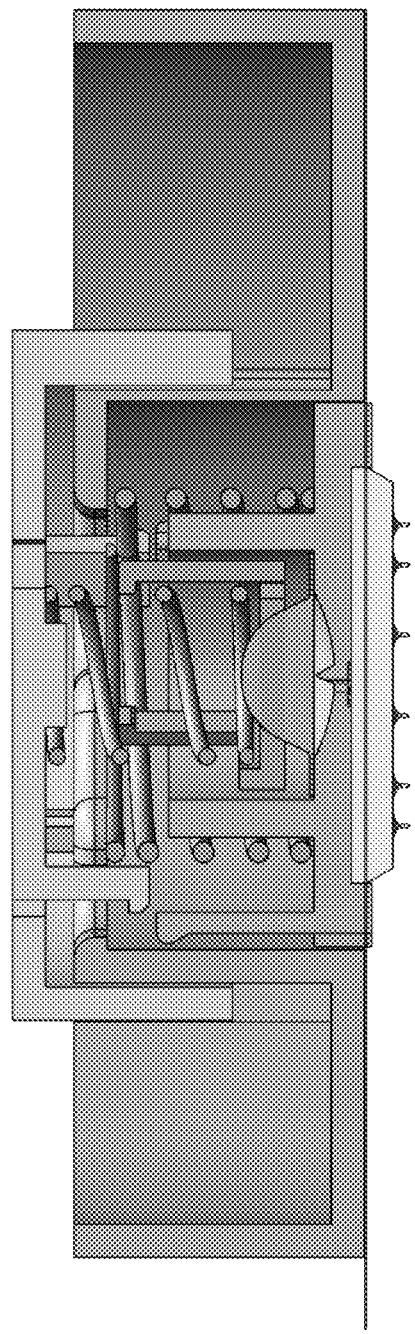
FIG. 15 is a cross-sectional view of a dermal patch wherein a pin of the dermal patch is in an extended position in accordance with an exemplary embodiment.

As depicted in FIG. 15, the actuator 200 may be pressed a second time with a second force to move the actuator 300 into a deployed pharmaceutical position. In the deployed pharmaceutical position, the latches 806 are no longer pressed into the top wall 304 and are able to release from the top wall 304 and when the latches 806 are released, the second biasing element 904 is able to expand thereby moving the pin 800 into a deployed position (FIG. 15). Stated another way. The top end 904a of the second biasing element pushes against the bottom surface 304b of the top wall 304 and the bottom end 904b of the second biasing element 904 pushes against the top surface 802a of the base 802 of the pin 800. Since the pin 800 is moveable and a user applies a downward force to the actuator 300, the force applied to the pin by the second biasing element 904 moves the pin 800 into the deployed position.

In the deployed position, the bottom surface 802b contacts the reservoir 600. The pin 800 compresses the sealed reservoir into the piercing element 510. When compressed into the piercing element 510, the reservoir 600 ruptures and the pharmaceutical stored in the reservoir 600 flow into opening 512. Since the opening 512 is in fluid communication with each of the microfluidic channels 514 which are each in communication with a needle 704, the pharmaceutical flows through the opening 512 and each of the microfluidic channels 514 and is delivered to the subject via a needle 704. While the pharmaceutical is being delivered to the subject, the first biasing element applies a continuous force to the mount 500 thereby ensuring the needles 704 stay within the skin of the subject during pharmaceutical delivery.

In some embodiments, after the pharmaceutical has been administered, the mount 500 may be retracted into the inner volume 222 of the frame 200 such that the needles 704 are removed from the subject and are completely disposed within the inner volume 222. In one embodiment, the mount 500 may be retracted by rotating or pulling the actuator 300 to retract the needles 704.

After the pharmaceutical has been delivered, the dermal patch 100 may be removed from the subject by peeling the dermal patch 100 off of the subject's skin.

Referring now to FIGS. 18-23, a dermal patch 1000 is shown in accordance with an exemplary embodiment. In this embodiment, the dermal patch 1000 includes the frame 200, the actuator 300, the adhesive layer 400, the mount 500, the needle cartridge 700, and the first biasing element 902. The dermal patch 1000 may be affixed to an arm of a subject as previously discussed herein with respect to the dermal patch 100 and the adhesive layer 400. Furthermore, the actuator 300 may be moved into the deployed needle position to cause the needles 704 to puncture the skin of a subject as previously discussed herein.

Figure 23:
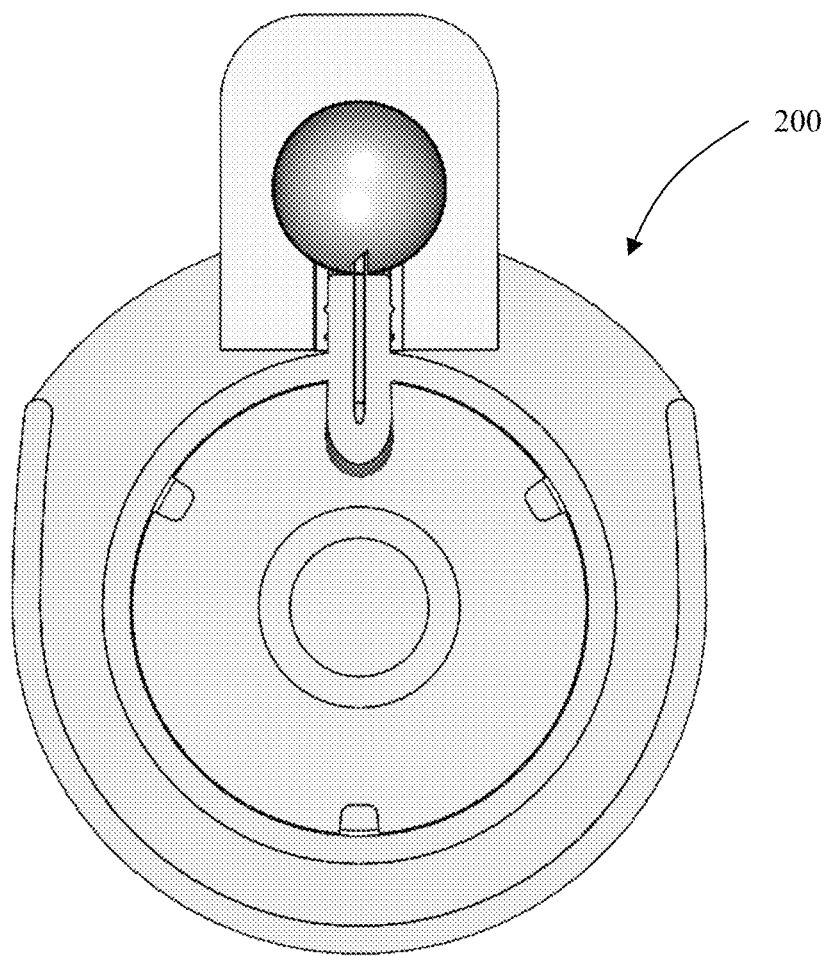
FIG. 23 depicts a dermal patch with an exposed slidable pharmaceutical reservoir and a U-shaped frame in accordance with an exemplary embodiment.

In this embodiment, the dermal patch 1000 includes a slidable pharmaceutical reservoir 1002 and the frame 200 is modified to support the slidable pharmaceutical reservoir 1002. The slidable pharmaceutical reservoir 1002 includes a sealed reservoir 1004, a push tab 1006, and a puncture element receiving chamber 1008. In another embodiment, as depicted in FIG. 23, the frame 200 of the dermal patch 1000 may be further modified such that the slidable pharmaceutical reservoir 1002 is exposed rendering it more accessible to a user.

The sealed reservoir 1004 may be in the form of a blister pack as previously discussed with reference to the reservoir 600. That is, the sealed reservoir 1004 retains a pharmaceutical. In some embodiments, the sealed reservoir 1004 is prefilled with a predetermined amount of a pharmaceutical. In such embodiments, the predetermined quantity of the pharmaceutical formulation is configured to provides a single dose of the pharmaceutical administration to a subject.

Figure 21:
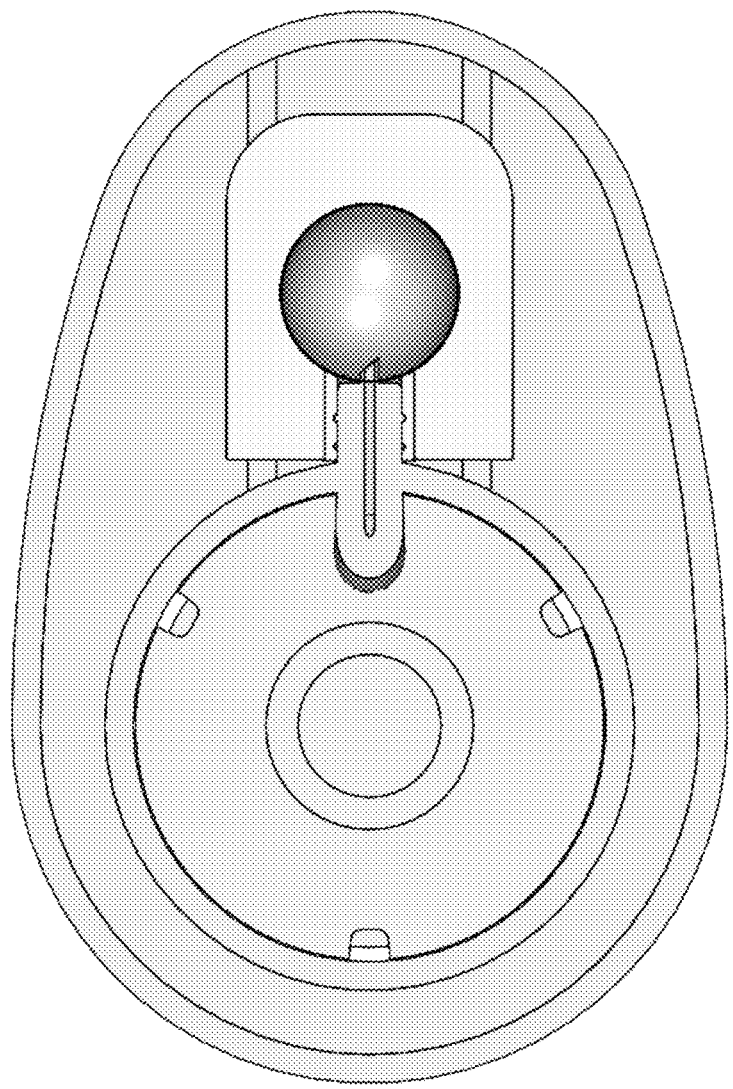
FIG. 21 depicts a dermal patch with a slidable pharmaceutical reservoir wherein the slidable pharmaceutical reservoir is in a deployed position.
Figure 22:
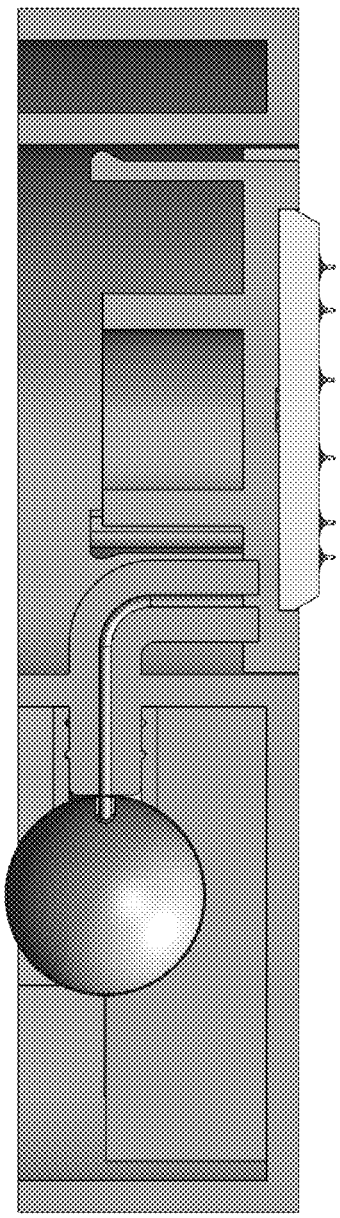
FIG. 22 is a cross-sectional view of a dermal patch with a slidable pharmaceutical reservoir in a deployed position in accordance with an exemplary embodiment.

The push tab 1006 is configured to allow a user to hold the push tab 1006 in order to move the slidable pharmaceutical reservoir 1002 from an undeployed position (FIG. 18) to a deployed position (FIG. 21).

In this embodiment, the frame 200 further includes a hollow puncturing element 1010 and the puncture element receiving 1008 is shaped to receive the hollow puncturing element 1010. The hollow puncturing element 1010 includes a protrusion 1012 that extends circumferentially around an outer wall of the hollow puncturing element 1010 and the puncture element receiving chamber 1008 includes a first groove 1014 and a second groove 1016 that extend circumferentially within the puncture element receiving chamber 1008. The first groove 1014 receives the protrusion 1012 when the slidable pharmaceutical reservoir 1002 is in the undeployed position and the second groove 1016 receives protrusion 1012 when the slidable pharmaceutical reservoir 1002 is in the deployed position.

The hollow puncturing element 1010 includes a hollow point 1018 for puncturing the sealed reservoir 1004 and a microfluidic channel 1020 in communication with the hollow point 1018. The microfluidic channel 1020 is in communication with the plurality of secondary microfluidic channels. As such, the microfluidic channel 1020 is in communication with each needle 704.

Figure 18:
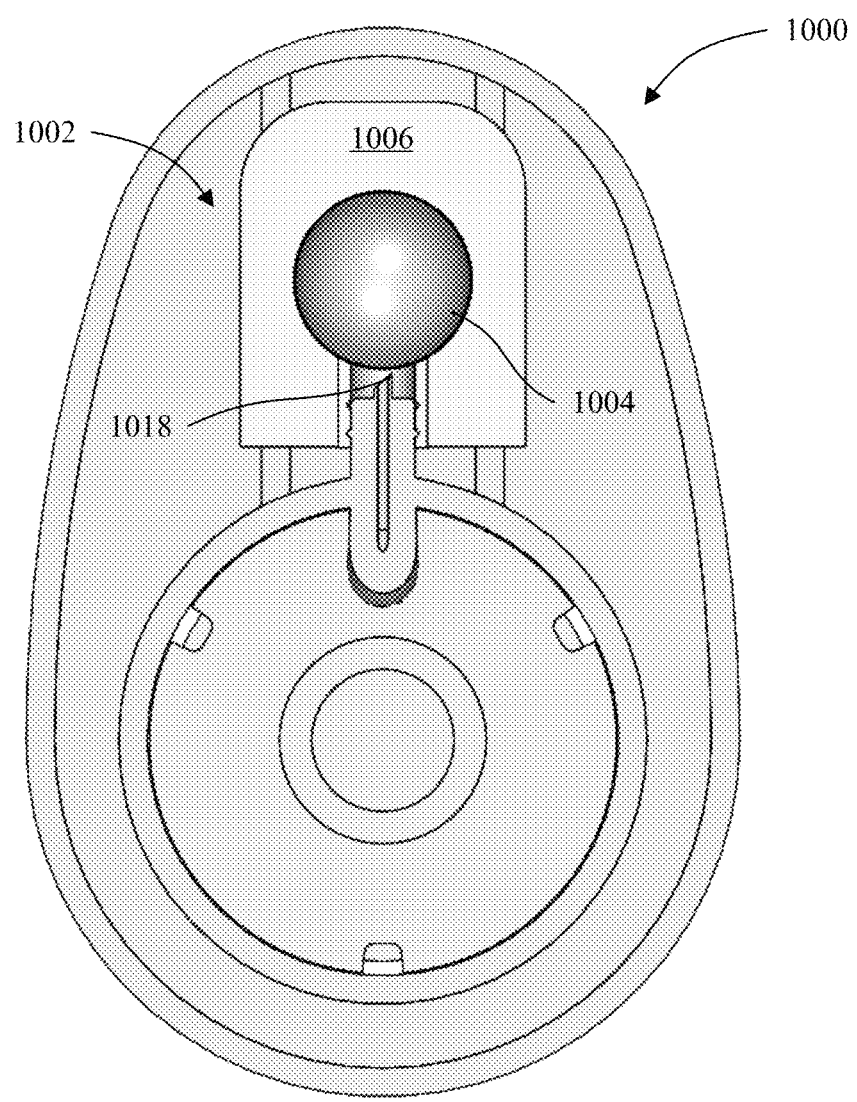
FIG. 18 depicts a dermal patch with a slidable pharmaceutical reservoir in accordance with an exemplary embodiment.
Figure 19:
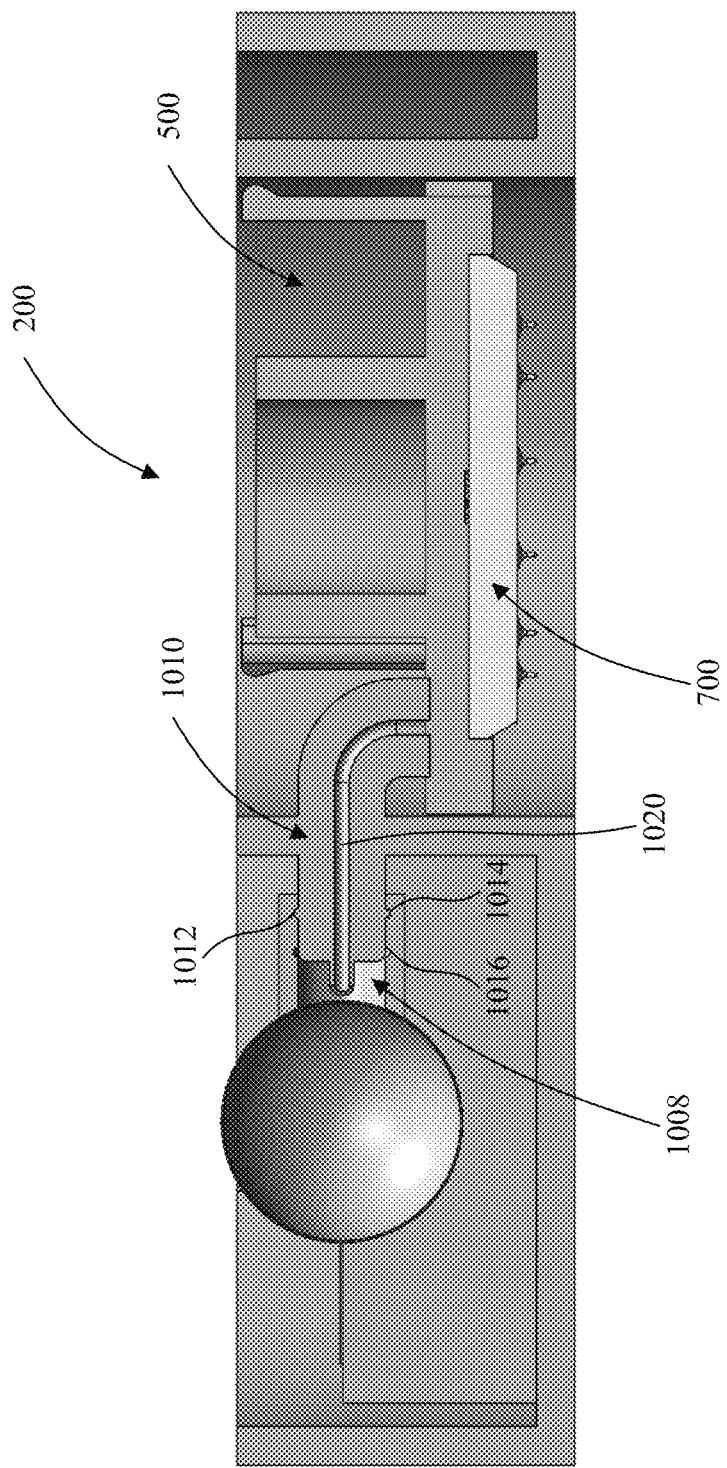
FIG. 19 is a cross-sectional view of a dermal patch with a slidable pharmaceutical reservoir in accordance with an exemplary embodiment.
Figure 20:
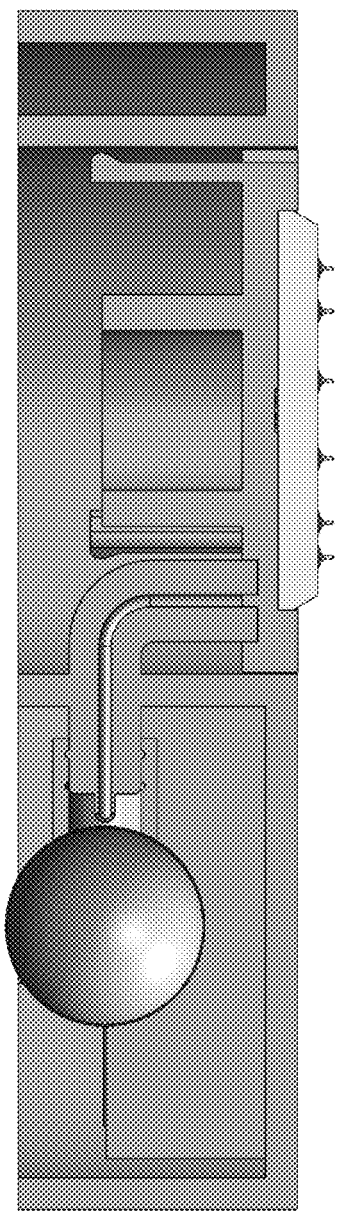
FIG. 20 is a cross-sectional view of a dermal patch with a slidable pharmaceutical reservoir wherein needles of the dermal patch are in an extended position in accordance with an exemplary embodiment.

In use, the dermal patch 1000 is adhered to the skin of a subject as previously discussed herein with respect to the dermal patch 100. Initially, as depicted in FIGS. 18 and 19, the mount 500 and the slidable pharmaceutical reservoir 1002 are in an undeployed position. In the undeployed position the needles 704 are in the retracted position as previously discussed herein. A user of the dermal patch 1000 then moves the actuator as previously discussed herein to cause the needles 704 to enter the extended position as previously discussed herein (FIG. 20). The user then moves the slidable pharmaceutical reservoir 1002 from the undeployed position to a deployed position via the push tab 1006. In the deployed position (FIG. 22), the hollow point 1018 punctures the sealed reservoir 1004 and the pharmaceutical stored therein enters the microfluidic channel 1020. Since the microfluidic channel 1020 is in communication with each of the microfluidic channels 514 of the mount 500 which are each in communication with a needle 704, the pharmaceutical flows through the microfluidic channel 1020 and each of the microfluidic channels 514 and is delivered to the subject via a needle 704. The user may squeeze the sealed reservoir 1004 in order to deliver all of the pharmaceutical to the subject. In some embodiments, the dermal patch 1000 includes a pin that prevents the slidable pharmaceutical reservoir 1002 from moving to the deployed position unless the dermal patch 1000 is in a proper orientation (i.e., positioned so that the hollow point 1018 is pointing upwards thereby ensuring all of the pharmaceutical may be delivered to the subject due to the orientation of the dermal patch 1000).

Referring now to FIGS. 24-27, a dermal patch 1100 in accordance with an embodiment. The dermal patch 1100 includes a housing 1102. The housing 1102 defines a vial chamber 1104 and a mount chamber 1104. The dermal patch 1100 further includes the mount 500 and the needle cartridge 700.

The vial chamber 1102 is dimensioned and shaped for receiving a vial 1106 that contains a pharmaceutical. The vial 1106 is sealed by a frangible membrane 1108. The mount chamber 1106 is shaped and dimensioned for retaining the mount 500.

The housing 1102 further includes a hollow puncturing element 1110. The hollow puncturing element 1110 includes a point 1112 for puncturing the membrane 1108 of the vial 1106. The housing 1102 further includes a microfluidic channel 1114 that is in communication with the point 1112. The microfluidic channel 1114 is also in communication with the plurality of microfluidic channels 514. As such, the microfluidic channel 1114 is in communication with each needle 704.

Figure 24:
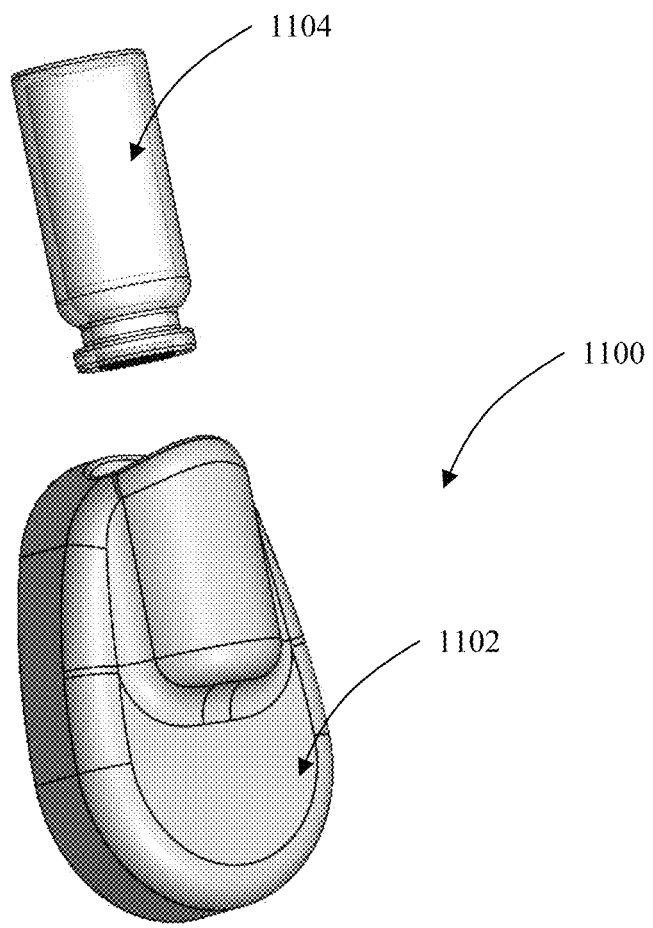
FIG. 24 depicts a dermal patch and a vial of containing a pharmaceutical in accordance with an exemplary embodiment.
Figure 25:
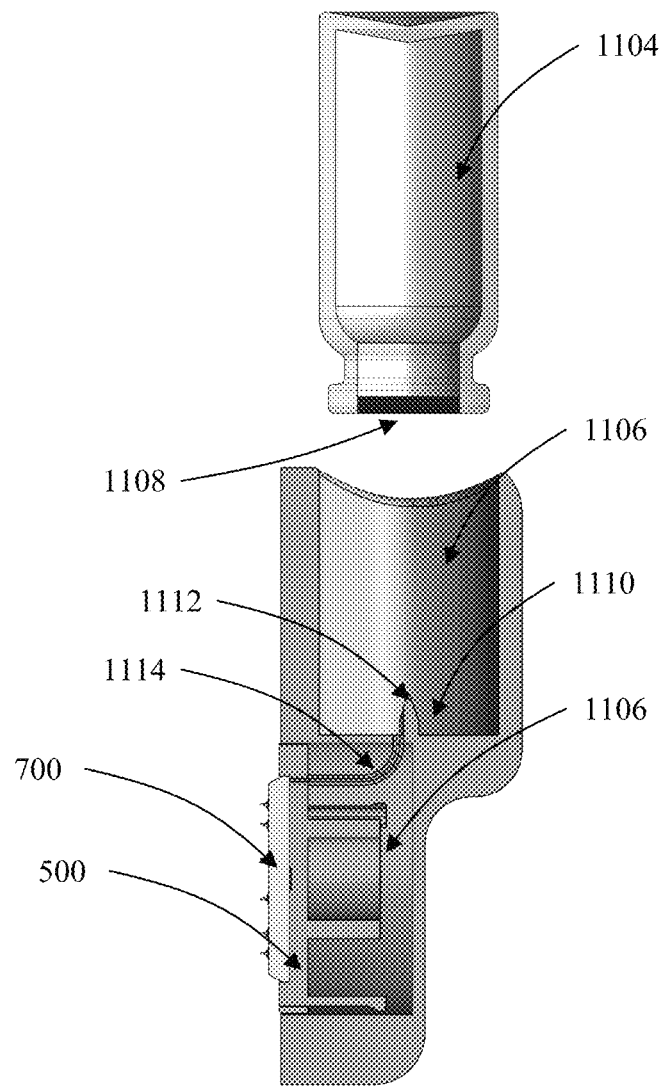
FIG. 25 is a cross section of a dermal patch and a vial of containing a pharmaceutical in accordance with an exemplary embodiment.
Figure 26:
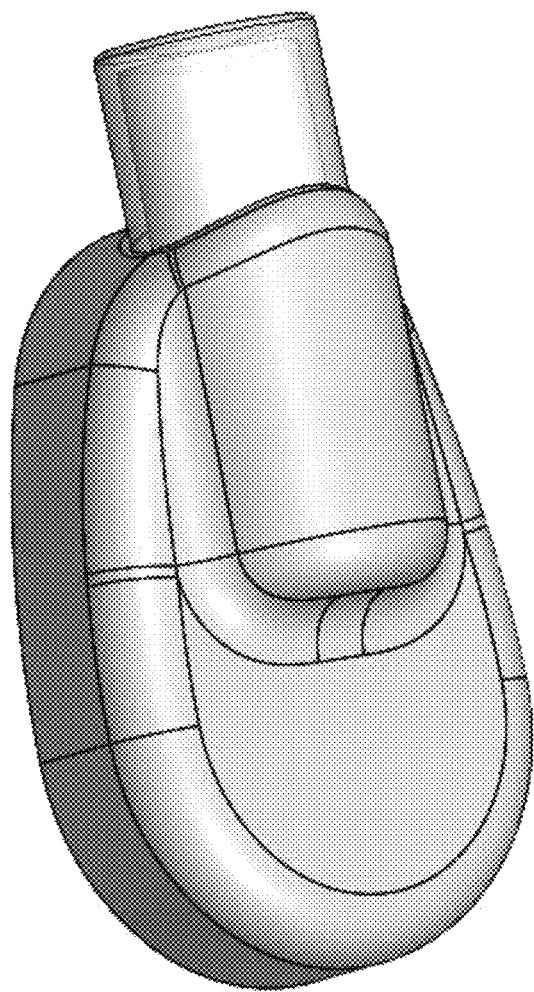
FIG. 26 depicts a vial of containing a pharmaceutical within a dermal patch in accordance with an exemplary embodiment.
Figure 27:
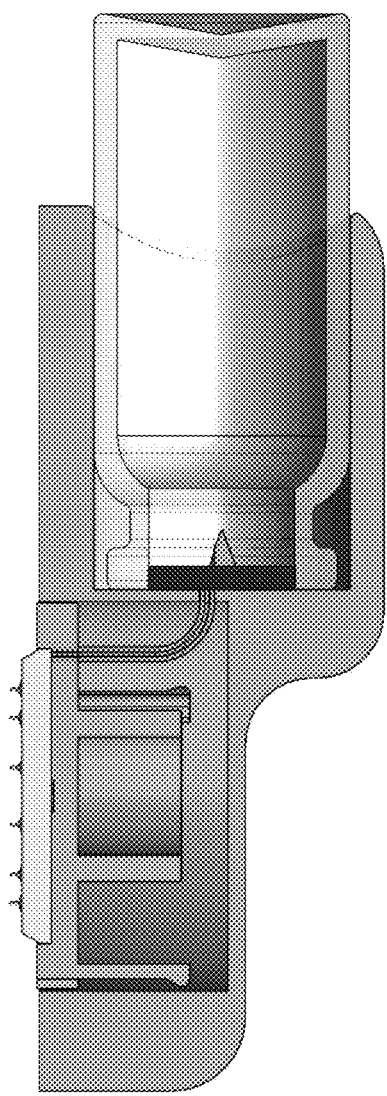
FIG. 27 is a cross section a vial of containing a pharmaceutical within a dermal patch in accordance with an exemplary embodiment.

In use, the dermal patch 1100 is adhered to the skin of a subject as previously discussed herein with respect to the dermal patch 100. As depicted in FIGS. 24-27, the needles 704 are in an extended position and as such, when the dermal patch 1100 is adhered to the subject's skin, the needles 704 puncture the skin of the subject. Initially, the vial 1106 is separate from the dermal patch 1100 (FIGS. 24 and 25). After the dermal patch 1100 has been adhered to the subject, the vial 1106 may be inserted into the dermal patch 1100. When inserted, the point 1112 punctures the membrane 1108 and gravity pulls the pharmaceutical into the microfluidic channel 1114. Since the microfluidic channel 1114 is in communication with each of the microfluidic channels 514 of the mount 500 which are each in communication with a needle 704, the pharmaceutical flows through the microfluidic channel 111 and each of the microfluidic channels 514 and is delivered to the subject via a needle 704.

The frame 200, the actuator 300, the mount 500, needle cartridge 700, the pin 800, and the housing 1100 may be formed from polymeric materials including, but not limited to, polymeric materials, i.e., polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymer. The slidable pharmaceutical reservoir 1002 may be formed of a plastic, aluminum or a combination thereof.

While the invention has been illustrated and described in detail in the drawings and foregoing description, such illustration and description are to be considered illustrative or exemplary and not restrictive; embodiments of the present disclosure are not limited to the disclosed embodiments. Other variations to the disclosed embodiments can be understood and effected by those skilled in the art in practicing embodiments of the present disclosure, from a study of the drawings, the disclosure, and the appended claims.

In the claims, the word "comprising" does not exclude other elements or steps, and the indefinite article "a" or "an" does not exclude a plurality. A single processor or other processing unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

What is claimed is:

1. A method for delivering a pharmaceutical to a subject, comprising:
    applying a dermal patch to a subject's skin,
        wherein the dermal patch includes a plurality of hollow needles each having a lumen, an actuator, a reservoir that includes a pharmaceutical, an opening for receiving the pharmaceutical from the reservoir and a plurality of fluidic channels each extending from said opening to a lumen of one of said plurality of hollow needles such that each of said plurality of fluidic channels delivers a portion of the pharmaceutical to the lumen of one of said plurality of hollow needles,
        wherein the plurality of needles is movable between an undeployed position and a deployed position to puncture the subject's skin,
    causing the plurality of needles to move from the undeployed position to the deployed position so as to puncture the skin of the subject, and
    subsequently actuating the actuator to cause the reservoir to release the pharmaceutical via said opening into the plurality of fluidic channels so as to deliver the pharmaceutical to the subject via the plurality of needles.

2. The method of claim 1, wherein the pharmaceutical comprises a vaccine.

3. The method of claim 1, wherein the dermal patch is a single-use dermal patch.

4. The method of claim 1, wherein said reservoir contains a quantity of the pharmaceutical suitable for a single fractional dose administration to the subject.

5. The method of claim 1, wherein the plurality of needles have a length in a range of about 100 microns to about 1600 microns.

6. The method of claim 1, wherein the plurality of needles is configured for any of intra-dermal and intra-muscular delivery of the pharmaceutical.

7. The method of claim 1, wherein the dermal patch further includes a pin and a piercing element, and wherein moving the actuator to the second position causes the pin to compress the reservoir into the piercing element thereby rupturing the reservoir to release the pharmaceutical.

8. The method of claim 1, wherein said subject is any of a human and an animal.

9. A dermal patch for delivering a pharmaceutical to a subject comprising:
a reservoir that includes a pharmaceutical,
an opening for receiving the pharmaceutical from the reservoir,
a plurality of hollow needles, each needle having a lumen,
a plurality of channels each extending from said opening to a lumen of one of said plurality of hollow needles such that each of said plurality of fluidic channels delivers a portion of the pharmaceutical to the lumen of one of said plurality of hollow needles, and
an actuator configured to move to a first position and move from the first position to a second position,
wherein in the first position, the actuator is configured to cause the plurality of needles to move from a retracted position to an extended position, and
wherein in the second position, the actuators is configured to cause the reservoir to release the pharmaceutical into the plurality of fluidic channels.

10. The dermal patch of claim 9, further comprising:
a pin, and
a piercing element,
wherein in the second position, the actuator is further configured to cause the pin to apply pressure to the reservoir thereby causing the reservoir to engage with the piercing element which ruptures the reservoir to release the pharmaceutical.

11. The dermal patch of claim 9, wherein said pharmaceutical comprises a vaccine.

12. The dermal patch of claim 9, wherein said is configured for intra-dermal administration of the pharmaceutical to the subject.

13. The dermal patch of claim 9, wherein the plurality of needles is configured for intra-muscular administration of the pharmaceutical to the subject.

14. The dermal patch of claim 9, wherein said dermal patch comprises a needle cartridge to which said plurality of needles is mounted.

15. The dermal patch of claim 14, wherein said dermal patch further comprises a mount to which said needle cartridge is coupled.

16. The dermal patch of claim 15, wherein said at least one actuator is operably coupled to said mount to move said mount so as to transition said plurality of needles from the retracted position to the extended position.

17. The dermal patch of claim 16, wherein said at least one actuator comprises an actuating element operably coupled to said mount for causing movement thereof.

18. The dermal patch of claim 17, further comprising a biasing element positioned between said actuating element and said mount for facilitating moving said mount.

19. The dermal patch of claim 9, further comprising an adhesive layer coupled to said dermal patch for attaching said dermal patch to a subject's skin.

20. The dermal patch of claim 9, wherein said dermal patch comprises an opening in a bottom surface thereof through which said plurality of needles can be extended to puncture the skin.

21. The dermal patch of claim 9, wherein said reservoir contains a quantity of the pharmaceutical suitable for a single-dose administration to a subject.

22. A dermal patch for delivering a pharmaceutical to a subject comprising: f
a sealed and slidable reservoir that contains a pharmaceutical,
an opening for receiving the pharmaceutical from the reservoir,
a push tab that is affixed to the reservoir and is configured to allow a user to move the reservoir from an undeployed position to a deployed position,
a hollow puncture element including a hollow point,
wherein the hollow point is configured to puncture the reservoir to release the pharmaceutical when the reservoir is in the deployed position,
a microfluidic channel in communication with the hollow point and configured to receive the released pharmaceutical,
a plurality of hollow needles each having a lumen that is in fluid communication with the microfluidic channel, and
a plurality of fluidic channels each extending from said opening to a lumen of one of said plurality of hollow needles such that each of said plurality of fluidic channels delivers a portion of the pharmaceutical to the lumen of one of said plurality of hollow needles,
wherein the plurality of needles and the puncture element are independent from one another,
wherein the plurality of needles is configured to move between a retracted position and a deployed position, and
wherein the plurality of needles is further configured to puncture the skin of a subject to provide a passageway for delivery of the released pharmaceutical to the subject via the lumens when the needles are in the deployed position.

23. The dermal patch of claim 22, wherein said reservoir comprises a blister pack.

24. The dermal patch of claim 22, wherein said blister pack contains a single fractional dose of the pharmaceutical.

25. A method for delivering a pharmaceutical to a subject, comprising:
applying a dermal patch to a subject's skin, wherein the dermal patch includes:
a plurality of hollow needles each having a lumen,
a reservoir that stores a pharmaceutical,
an opening for receiving the pharmaceutical from the reservoir,
a plurality of fluidic channels each extending from said opening to a lumen of one of said plurality of hollow needles such that each of said plurality of fluidic channels delivers a portion of the pharmaceutical to the lumen of one of said plurality of hollow needles,
a pin,
a latch for retaining the pin in an undeployed position,
actuating the plurality of hollow needles to puncture the subject's skin, and
releasing the latch to deploy the pin to rupture the reservoir thereby releasing the stored pharmaceutical from the reservoir for delivery via the lumens of the plurality of needles to the subject.

26. The method of claim 1, wherein the plurality of fluidic channels extends radially from the opening to the plurality of needles.

27. The dermal patch of claim 9, wherein the plurality of fluidic channels extends radially from the opening to the plurality of needles.

28. The dermal patch of claim 22, wherein the plurality of fluidic channels extends radially from the opening to the plurality of needles.

29. The method of claim 25, wherein the plurality of fluidic channels extends radially from the opening to the plurality of needles.

\* \* \* \* \*